US008779094B2

(12) United States Patent
Johnston et al.

(10) Patent No.: US 8,779,094 B2
(45) Date of Patent: Jul. 15, 2014

(54) LOW VISCOSITY HIGHLY CONCENTRATED SUSPENSIONS

(75) Inventors: Keith P. Johnston, Austin, TX (US); Maria Andrea Mazuski, Austin, TX (US); Joshua Engstrom, Spotswood, NJ (US); Miguel Angelo Rodrigues, Quinta do Conde (PT)

(73) Assignee: Board of Regents, The University of Texas System, Austin, TX (US)

( * ) Notice: Subject to any disclaimer, the term of this patent is extended or adjusted under 35 U.S.C. 154(b) by 84 days.

(21) Appl. No.: 13/129,283

(22) PCT Filed: Nov. 10, 2009

(86) PCT No.: PCT/US2009/063852
§ 371 (c)(1),
(2), (4) Date: Jul. 27, 2011

(87) PCT Pub. No.: WO2010/056657
PCT Pub. Date: May 20, 2010

(65) Prior Publication Data
US 2011/0280864 A1    Nov. 17, 2011

Related U.S. Application Data

(60) Provisional application No. 61/115,080, filed on Nov. 16, 2008.

(51) Int. Cl.
*C07K 16/00* (2006.01)

(52) U.S. Cl.
USPC .................. 530/350; 530/380; 530/387.1

(58) Field of Classification Search
None
See application file for complete search history.

(56) References Cited

U.S. PATENT DOCUMENTS

| | | |
|---|---|---|
| 3,869,549 A | 3/1975 | Geller |
| 4,310,516 A | 1/1982 | Chang et al. |
| 4,588,614 A | 5/1986 | Lauchenauer |
| 4,594,108 A | 6/1986 | Greminger, Jr. et al. |
| 5,300,302 A | 4/1994 | Tachon et al. |
| 5,352,662 A | 10/1994 | Brooks et al. |
| 5,411,951 A | 5/1995 | Mitchell |
| 5,512,293 A | 4/1996 | Landrau et al. |
| 5,540,912 A | 7/1996 | Roorda et al. |
| 5,571,525 A | 11/1996 | Roorda et al. |
| 5,614,221 A | 3/1997 | Fjellstrom |
| 5,635,213 A | 6/1997 | Nystrom et al. |
| 7,258,869 B1 | 8/2007 | Berry et al. |
| 7,374,782 B2 | 5/2008 | Brown |
| 7,651,770 B2 | 1/2010 | Berkland et al. |
| 2004/0022861 A1 | 2/2004 | Williams et al. |
| 2004/0151779 A1 | 8/2004 | Maskiewicz et al. |
| 2004/0197324 A1* | 10/2004 | Liu et al. ............ 424/130.1 |
| 2005/0048002 A1* | 3/2005 | Rabinow et al. ......... 424/46 |
| 2005/0053666 A1 | 3/2005 | Tzannis et al. |
| 2006/0024379 A1 | 2/2006 | Brown et al. |
| 2006/0193918 A1* | 8/2006 | Rohloff et al. ........... 424/486 |
| 2007/0015689 A1 | 1/2007 | Rohloff et al. |
| 2007/0207210 A1 | 9/2007 | Brown et al. |
| 2009/0104271 A1 | 4/2009 | O'Hagan et al. |
| 2009/0191277 A1 | 7/2009 | Aimi |
| 2009/0274765 A1 | 11/2009 | Beduneau et al. |
| 2009/0304599 A1 | 12/2009 | Aimi et al. |
| 2010/0009007 A1 | 1/2010 | Darvari et al. |
| 2010/0047903 A1 | 2/2010 | Piran et al. |
| 2010/0158899 A1 | 6/2010 | Andya et al. |
| 2010/0226928 A1 | 9/2010 | Dani |

FOREIGN PATENT DOCUMENTS

| | | |
|---|---|---|
| EP | 0379147 A2 | 7/1990 |
| WO | 95/34285 A1 | 12/1995 |
| WO | 96/40049 A1 | 12/1996 |
| WO | 98/00152 A1 | 1/1998 |
| WO | 98/00157 A1 | 1/1998 |
| WO | 98/00158 A1 | 1/1998 |
| WO | 98/16250 A1 | 4/1998 |
| WO | 00/45790 A2 | 8/2000 |
| WO | 2004/112747 A2 | 12/2004 |
| WO | 2005/035088 A3 | 4/2005 |
| WO | 2009/002874 A1 | 12/2008 |
| WO | 2009/137112 A1 | 11/2009 |

OTHER PUBLICATIONS

Bagaria, J.P., "Protein-nanoparticle constructs for intracelluar delivery", Master Thesis in NTNU Norwegian University of Science Technology, Feb. 18, 2011, 108 pages.
Escaig, J., "New instruments which facilitate rapid freezing at 83 K and 6 K." *Journal of Microscopy.* (Oxford, United Kingdom) 126:221-230 (1982).
Gilkey, J.C. et al., "Advances in ultrarapid freezing for the preservation of cellular ultrastructure." *Journal of Electron Microscopy Technique* 3:177-210 (1986).
International Preliminary Report on Patentability and Written Opinion dated Dec. 22, 2009 for International Application No. PCT/US2008/067766, 7 pages.
International Preliminary Report on Patentability and Written Opinion dated Sep. 10, 2013 for International Application No. PCT/US2012/028640, 8 pages.
International Search Report dated Sep. 5, 2008 for International Application No. PCT/US2008/067766, 1 page.
International Search Report dated Sep. 10, 2012 for International Application No. PCT/US2012/028640, 5 pages.

(Continued)

*Primary Examiner* — Yunsoo Kim
(74) *Attorney, Agent, or Firm* — Kilpatrick Townsend & Stockton LLP

(57) ABSTRACT

The present invention also provides a high concentration low viscosity suspension of an pharmaceutically acceptable solvent with one or more sub-micron or micron-sized non-crystalline particles comprising one or more proteins or peptides. Optionally one or more additives in the pharmaceutically acceptable solvent to form a high concentration low viscosity suspension with a concentration of at least 20 mg/ml and a solution viscosity of between 2 and 100 centipoise that is suspendable upon shaking or agitation, wherein upon delivery the one or more sub-micron or micron-sized peptides dissolves and do not form peptide aggregates syringeable through a 21 to 27-gauge needle.

14 Claims, 11 Drawing Sheets

(56) References Cited

OTHER PUBLICATIONS

Johnston, K.P. et al., "Concentrated dispersions of equilibrium protein nanoclusters that reversibily dissociate into active monomers",*ACS Nano*, 2013 6(2):1357-1369.

Maa, Y.F. et al., "Spray freeze-drying of biopharmaceuticals: applications and stability considerations." in: H. R. Costantino and M. J. Pikal (Eds), Biotechnology: Pharmaceutical Aspects. 2. Lyophilization of Biopharmaceuticals, vol. 2 (H. R. Costantino and M. J. Pikal, eds), American Association of Pharmaceutical Scientists, Arlington, 2004, pp. 519-561.

Overhoff et al. "Novel ultra-rapid freezing particle engineering process for enhancement of dissolution rates of poorly water-soluble drugs", European Journal of Pharmaceutics and Biopharmaceutics vol. 65, No. 1, Jan. 2007, pp. 55-67.

Brown, L. R., "Commercial challenges of protein drug delivery." *Expert Opinion on Drug Delivery* 2005, 2(1):29-42.

"High Concetration Monoclonal Antibody Suspensions for Subcutaneous Injection" presented by Larry Brown et al. Baxter Healthcare Corporation Mar. 2007, 1 page. (Abstract).

Chen, G. et al., "Injectable nonaqueous suspension of highly concentrated proteins for non-IV administration.", AAPS Annual Meeting and Exposition, Nashville, TN, 2005; The AAPS Journal: Nashville, TN, 2005, 1 page. (Abstract).

International Preliminary Report on Patentability and Written Opinion dated May 17, 2011 for International Application No. PCT/US2009/063852, 4 pages.

International Search Report dated Jul. 27, 2010 for International Application No. PCT/US2009/063852, 3 pages.

"Highly Concentrated Dispersions of Stable Submicron Therapeutic Protein Particles for Subcutaneous Injection." presented by Keith P. Johnston et al. Department of Chemical Engineering, University of Texas—Austin, 2011, 1 page. (Abstract).

Kanai, S. et al., "Reversible Self-Association of a Concentrated Monoclonal Antibody Solution Mediated by Fab-Fab Interaction That Impacts Solution Viscosity.", *Journal of Pharmaceutical Sciences* 2008, 97(10):4219-4227.

Martins, S. et al., "Lipid-based colloidal carriers for peptide and protein delivery-liposomes versus lipid nanoparticles", *International Journal of Nanomedicine* 2007, 2(4):595-607.

Miller, M. A., "Highly Concentrated, Nanoclusters of Self-crowded Monoclonal Antibodies for Low Viscosity, Subcutaneous Injections.", Ph. D. Thesis. Department of Chemical Engineering. Austin, The University of Texas at Austin, May 2011, 328 pages.

Miller, M. A. et al., "Low Viscosity Highly Concentrated Injectable Nonaqueous Suspensions of Lysozyme Microparticles", *Langmuir* 2010, 26(2):1067-1074.

Yu, Z. et al., "Spray freezing into liquid versus spray-freeze drying: Influence of atomization on protein aggregation and biological activity", *European Journal of Pharmaceutical Sciences* 2006, 27:9-18.

\* cited by examiner

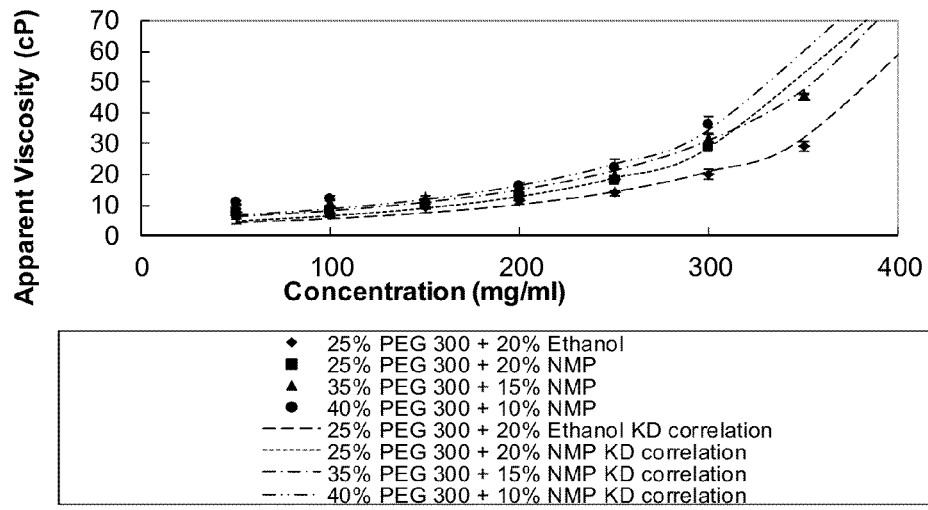
FIGURE 6
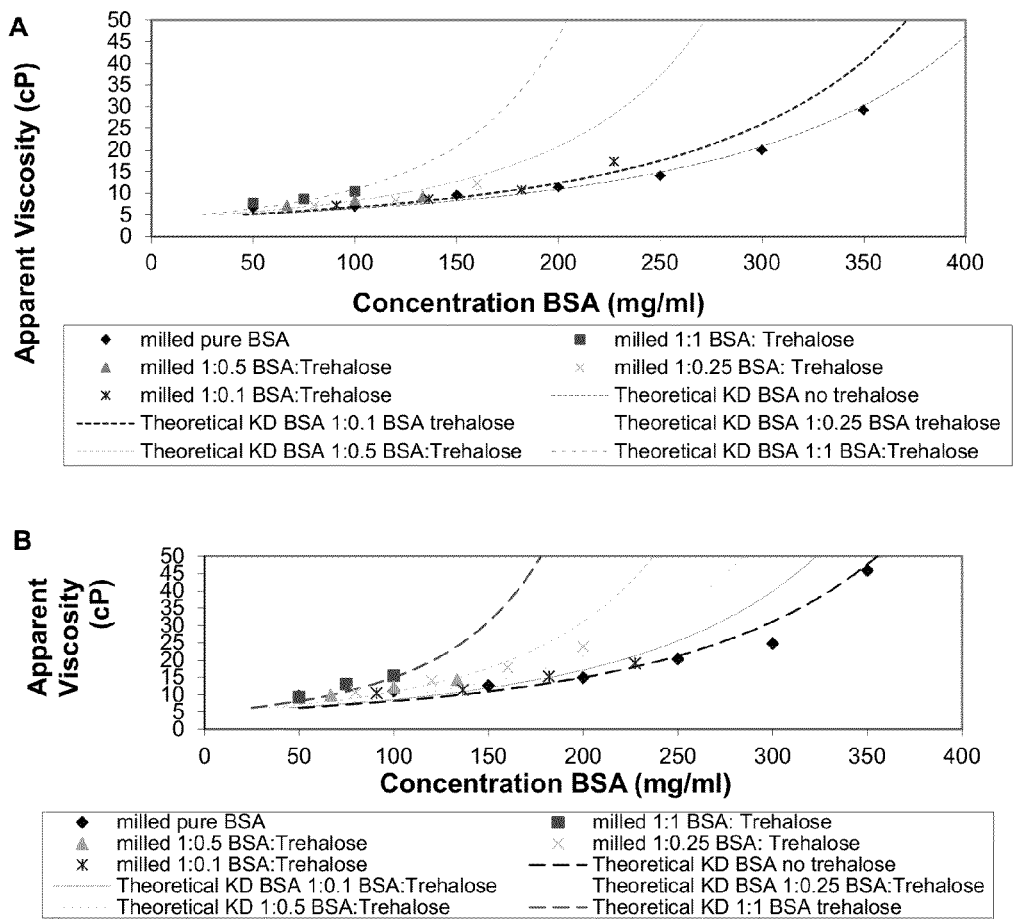
FIGURE 7A and B

LOW VISCOSITY HIGHLY CONCENTRATED SUSPENSIONS

CROSS-REFERENCE TO RELATED APPLICATIONS

This application claims priority to U.S. Provisional Application Ser. No. 61/115,080, filed Nov. 16, 2008 the contents of which is incorporated by reference herein in its entirety.

STATEMENT OF FEDERALLY FUNDED RESEARCH

None.

TECHNICAL FIELD OF THE INVENTION

The present invention relates in general to the field of protein storage and delivery, and more particularly, to novel compositions and methods of making highly concentrated protein suspension and precursors thereof.

BACKGROUND ART

Without limiting the scope of the invention, its background is described in connection with the concentration of proteins. The use of proteins and other polypeptides for therapeutics is on the rise in recent years as a way to expand and better treat patients since they are viewed to be less toxic and behave more predictably in vivo than other classes of drugs not naturally found in the body. Delivery of protein therapeutics has been limited primarily to dilute large volume intravenous injections to deliver the high dose required (100-1000 mg) and to avoid physical and chemical instabilities of proteins at high concentrations. A potentially less invasive method of administration is subcutaneous injection. Since the injection volume is limited to 1.5 ml, the concentration of the protein therapeutic is often substantially above 100 mg/ml. In addition to polypeptide stability, another major concern is the dramatic increase in viscosity for solution concentrations greater than 100 to 400 mg/ml due to protein interactions. If the primary interactions are attractive protein-protein interactions due to electrostatics, this increase in viscosity can been avoided by adding sodium chloride to increase the ionic strength of the solution and by varying the buffer species and pH of the solution. At these high concentrations, large excipient concentrations are often needed to protect against denaturation. An alternative approach would be to form a suspension of an insoluble protein in a non-aqueous solvent. The viscosity of highly concentrated suspensions can be much lower than for solutions and require smaller excipient levels to stabilize the protein. However, for successful delivery with concentrated suspensions, the particle size and suspension uniformity must be controlled in order to administer an accurate and uniform dose.

To date, there are relatively few examples of suspensions of proteins in non-aqueous media for medicinal purposes. Highly viscous suspensions of bovine somatotropin, marketed to increase milk production in dairy cows, and a bovine growth hormone releasing factor analog, used to release somatotropin from the cow's pituitary gland, are formulated in sesame oil and Miglyol oil, respectively. These viscous suspensions require a large 14-16 gauge needle for injection, whereas the preferred needle size for humans is between 25-gauge and 27-gauge. In addition, a few non-aqueous injections have been formulated as extended release formulations for the peptide insulin and very stable proteins such as protein C and a proprietary monoclonal antibody with the aid of viscosity enhancers and gel forming polymers in the presence of diluents such as benzyl benzoate or benzyl alcohol. However, these formulations are syringeable only with a larger 21-gauge needle causing considerable pain upon injection leading to non-compliance and the high levels of excipients reduce the overall concentration of the protein in the formulation. Another option is to crystallize the protein or monoclonal antibody and form an aqueous suspension of the crystals. This approach has been shown for three monoclonal antibodies and insulin. However, crystallization of high molecular weight proteins can be very difficult due to the high degree of segmental flexibility, and is more feasible for small peptides that have a much lower degree of flexibility.

DISCLOSURE OF THE INVENTION

The present invention provides a method of making a high concentration low viscosity protein or peptide suspension by forming one or more sub-micron or micron-sized particles comprising one or more proteins or peptides, adding optionally one or more additives to the one or more sub-micron or micron-sized particles and suspending the one or more sub-micron or micron micron-sized particles in a pharmaceutically acceptable solvent to form a high concentration low viscosity suspension with a concentration of at least 20 mg/ml and a solution viscosity of between 2 and 100 centipoise that is suspendable upon shaking or agitation, wherein upon delivery the one or more sub-micron or micron-sized peptides dissolves and do not form peptide aggregates or only a small fraction of aggregates and is syringeable through a 21 to 27-gauge needle. The pharmaceutically acceptable solvent may be a pharmaceutically acceptable aqueous solvent, a pharmaceutically acceptable non-aqueous solvent or combination.

In addition, the one or more micron-sized peptide particles are formed in a dosage container and may be delivered directly from the dosage container that is a vial, an ampule, a syringe or a bulk container. The one or more micron-sized peptide particles may be made by milling, precipitation, dialysis, sieving, spray drying, lyophilization, spray freeze drying, spray freezing into liquids, thin film freezing, or freezing directly in a dosage container. The one or more additives may be part of the one or more sub-micron or micron-sized particles, the a high concentration low viscosity suspension or both.

The present invention also provides a high concentration low viscosity suspension of an pharmaceutically acceptable solvent with one or more sub-micron or micron-sized non-crystalline particles comprising one or more proteins or peptides. Optionally one or more additives in the pharmaceutically acceptable solvent to form a high concentration low viscosity suspension with a concentration of at least 20 mg/ml and a solution viscosity of between 2 and 100 centipoise that is suspendable upon shaking or agitation, wherein upon delivery the one or more sub-micron or micron-sized peptides dissolves and do not form peptide aggregates or only a small fraction of aggregates syringeable through a 21 to 27-gauge needle. The pharmaceutically acceptable solvent may be a pharmaceutically acceptable aqueous solvent, a pharmaceutically acceptable non-aqueous solvent or combination. In addition, the one or more micron-sized peptide particles are formed in a dosage container and may be delivered directly from the dosage container that is a vial, an ampule, a syringe or a bulk container. The one or more micron-sized peptide particles may be made by milling, precipitation, dialysis, sieving, spray drying, lyophilization, spray freeze drying, spray freezing into liquids, thin film freezing, or freezing directly in a dosage container. The one or more additives may be part of the one or more sub-micron or micron-sized particles, the a high concentration low viscosity suspension or both.

The present invention provides a single dose high concentration low viscosity suspension in a single dose container. The single dose container includes a pharmaceutically acceptable solvent disposed in the single dose container, wherein the pharmaceutically acceptable solvent is selected from an aqueous solvent, a non-aqueous solvent or combination thereof and one or more sub-micron or micron-sized non-crystalline particles disposed in the single dose container, wherein the one or more sub-micron or micron-sized non-crystalline particles comprising one or more proteins or peptides. In addition, one or more additives may be optionally disposed in the single dose container to form a high concentration low viscosity suspension with a a concentration of at least 20 mg/ml and a solution viscosity of between 2 and 100 centipoise syringeable through a 21 to 27-gauge needle.

DESCRIPTION OF THE DRAWINGS

For a more complete understanding of the features and advantages of the present invention, reference is now made to the detailed description of the invention along with the accompanying figures and in which:

FIG. 6 is a graph of the apparent viscosity of aqueous suspensions with PEG 300 and organic additives in 150 mM pH 4.7 acetate buffer with added NaCl to 154 mM ionic strength.

FIGS. 7A and 7B are graphs that show the apparent viscosities of milled BSA and trehalose at various ratios in 150 mM pH 4.7 acetate buffer along with the theoretical viscosity as calculated from the Krieger-Dougherty equation using the [$\eta$] of the pure milled particles in a) 25% PEG 300 20% Ethanol and b) 35% PEG 300 and 15% NMP.

Figure 1:
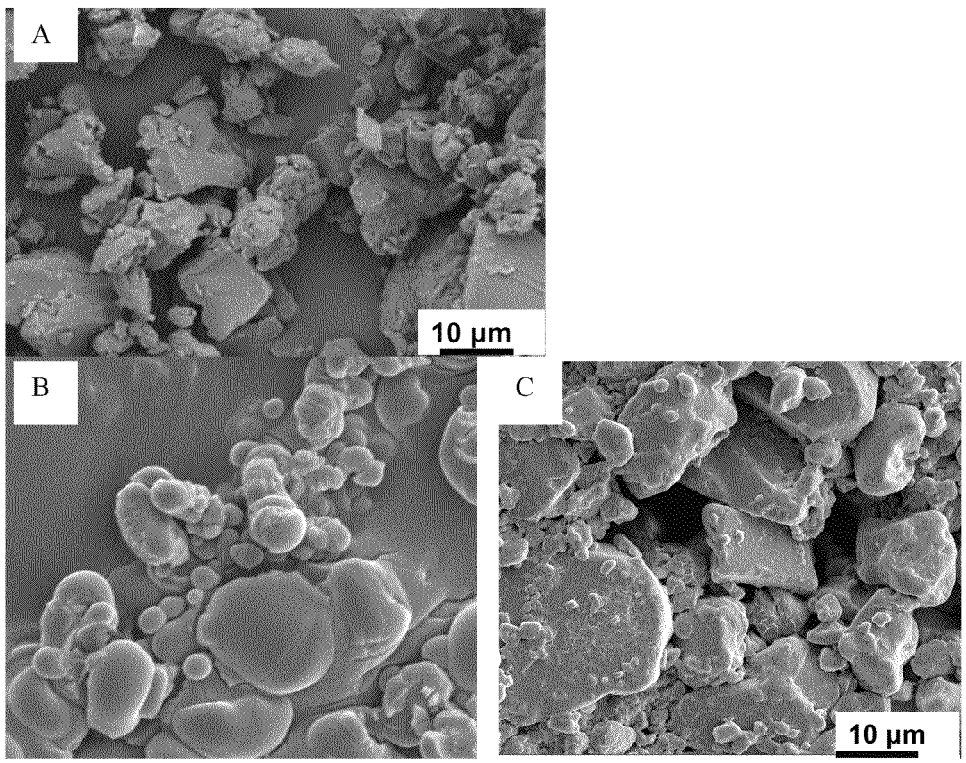
FIGS. 1A-C are SEM images of particles made by the process of one embodiment of the present invention.

FIG. 19A-19D Volume size distributions of the protein particles produced by Film Freezing in Vials in the conditions described in Table 2.

FIG. 20 shows a 4 ml of lysozyme solution (20 mg/ml) in water were frozen by film freezing inside the vial.

FIG. 21 shows a 2 ml of hemoglobin solution (150 mg/ml) in water was frozen by film freezing inside the vial.

DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "high protein concentration" refers to liquids, gels, hydrogels or gel-like compositions with a protein concentration of greater than 100 mg/ml.

As used herein, the term "non-aggregating" or "not aggregating" or "not aggregated" refers to protein particles that remain in suspension despite being provided in the form of a high protein concentration, e.g., a protein concentration greater than 100 mg/ml.

As used herein, the term "syringable" refers to a final composition for delivery to a subject that is sufficiently fluid to be flowable. For example, a composition that is "syringable" has a low enough viscosity to load the syringe and inject a subject from the syringe without undue force.

As used herein, the term "non-settling" or "redispersible" refers to a composition that remains in solution phase (i.e., they do not sediment) after an extended period of time, e.g., 1 hour, 2 hours, 1 day, 3 days, 5 days, 1 week, 1 month, 3 months, 6 months, 1 year or more. For example, a composition is "re-dispersible" is upon re-dispersion it does not flocculate so quickly as to prevent reproducible dosing of a drug.

As used herein, the terms "protein(s)," "polypeptide(s)" and "peptide(s)" refers to a polymer composition formed from the linking amino acids into a chain of various lengths.

As used herein, the term "additive(s)" refers to salts, sugars, organics, buffers, polymers and other compositions that include: Disodium edetate, Sodium chloride, Sodium citrate, Sodium succinate, Sodium hydroxide, Sodium glucoheptonate, Sodium acetyltryptophanate, Sodium bicarbonate, Sodium caprylate, Sodium pertechnetate, sodium acetate, sodium dodecyl sulfate, aluminum hydroxide, aluminum phosphate, ammonium citrate, calcium chloride, calcium, potassium chloride, potassium sodium tartarate, zinc oxide, zinc, stannous chloride, magnesium sulfate, magnesium stearate, titanium dioxide, DL-lactic/glycolic acids, asparagine, L-arginine, arginine hydrochloride, adenine, histidine, glycine, glutamine, glutathione, imidazole, protamine, protamine sulfate, phosphoric acid, Tri-n-butyl phosphate, ascorbic acid, cysteine hydrochloride, hydrochloric acid, hydrogen citrate, trisodium citrate, guanidine hydrochloride, mannitol, lactose, sucrose, agarose, sorbitol, maltose, trehalose, surfactants, polysorbate 80, polysorbate 20, poloxamer 188, sorbitan monooleate, triton n101, m-cresol, benzyl alcohol, ethanolamine, glycerin, phosphorylethanolamine, tromethamine, 2-phenyloxyethanol, chlorobutanol, dimethylsulfoxide, N-methyl-2-pyrrolidone, propyleneglycol, Polyoxyl 35 castor oil, methyl hydroxybenzoate, tromethamine, corn oil-mono-di-triglycerides, poloxyl 40 hydrogenated castor oil, tocopherol, n-acetyltryptophan, octa-fluoropropane, castor oil, polyoxyethylated oleic glycerides, polyoxytethylated castor oil, phenol (antiseptic), glyclyglycine, thimerosal (antiseptic, antifungal), Parabens (preservative), Gelatin, Formaldehyde, Dulbecco's modified eagles medium, Hydrocortisone, Neomycin, Von Willebrand factor, Gluteraldehyde, Benzethonium chloride, White petroleum, p-aminopheyl-p-anisate, monosodium glutamate, beta-propiolactone, Acetate, Citrate, Glutamate, Glycinate, Histidine, Lactate, Maleate, Phosphate, Succinate, Tartrate, Tris, Carbomer 1342 (copolymer of acrylic acid and a long chain alkyl methacrylate cross-linked with allyl ethers of pentaerythritol), Glucose star polymer, Silicone polymer, Polydimethylsiloxane, Polyethylene glycol, carboxymethylcellulose, Poly(glycolic acid), Poly(lactic-co-glycolic acid), Polylactic acid, Dextran 40, Poloxamers (triblock copolymers of ethylene oxide and propylene oxide), For highly concentrated protein suspensions in non-aqueous solvents, the Krieger-Dougherty equation can be used to correlate the relative viscosity of a suspension $\eta$ over that of a solution $\eta_o$ to the volume fraction of particles $\phi$ (Eq. 1).

$$\frac{\eta}{\eta_o} = \left[1\left(\frac{\phi}{\phi_{max}}\right)\right]^{-[\eta]\phi_{max}} \quad \text{Eq. 1}$$

The intrinsic viscosity, $[\eta]$ approaches 2.5, the Einstein value, assuming non-interacting, spherical particles with only excluded volume interactions. However, $[\eta]$ increases upon solvation of the particles, deviation from a spherical shape and electrostatic interactions that produce primary, secondary and tertiary electroviscous effects. For the non-aqueous protein suspensions demonstrated previously, $[\eta]$ of approximately 2.5 indicated a lack of solvation, shape and electroviscous effects on the viscosity of lysozyme milled particles. However, non-aqueous solvents can sometimes cause pain on injection and delayed and slowed release of the particles. Consequently, aqueous-based suspensions of highly concentrated and molecularly stable, protein particles would be an attractive alternative to non-aqueous suspensions.

Therapeutic proteins may be designed for high solubilities in aqueous media in the range of 100 mg/ml, for example, for the model protein BSA. Thus, the solubilities must often be decreased significantly, in order to form a suspension of micron-sized particles. Precipitant that can decrease the solubility of a protein in water may be separated into three categories; salts, polymers and water-soluble organics. Salts may decrease the solubility of a protein by competing for waters of hydration as well as ion binding to produce stronger interactions between protein molecules. Salts also reduce electrostatic repulsion by decreasing the thickness of the double layer. However, a total ionic strength of around 154 mM, the tonicity of the blood, is typically recommended to prevent pain upon injection. Polymers, most commonly polyethylene glycol (PEG), which are preferentially excluded from the protein surface, produce depletion attraction causing precipitation. PEG is also known to increase the thermal stability of a protein. Furthermore, it is an acceptable excipient for sub-cutaneous injection. Water-soluble organic additives, such as ethanol and n-methyl-2-pyrrolidone (NMP), decrease protein solubility by lowering the dielectric constant and by excluded volume effects resulting from their exclusion from the protein surface.

The objective of this study was to form low viscosity (<50 cP), highly concentrated (100 to 350 mg/ml) aqueous suspensions of sub-micron to micron-sized particles of the model protein bovine serum albumin (BSA) suitable for subcutaneous delivery. Precipitants, known to reduce the solubility of proteins included combinations of ammonium sulfate (a representative salt), PEG300 (a low molecular weight polymer), and ethanol and N-methyl-2-pyrrolidone (NMP). Two key factors influence the viscosity of the suspension at a given volume fraction of protein: the initial viscosity of the solution without protein and the intrinsic viscosity with protein present. Milled particles smaller than 37 μm of BSA were suspended in a variety of aqueous-based solvents to characterize these competing effects. In many cases, the concentrations of additives were within pharmaceutically acceptable limits. The apparent viscosity of the suspension at various particle concentrations is correlated with the Krieger-Dougherty equation to determine the intrinsic viscosity. The intrinsic viscosity was used to characterize interparticle interactions including electroviscous and solvation interactions. A variety of low viscosity, highly concentrated (up to 350 mg/ml) aqueous-based suspensions comprising pharmaceutically relevant additives are reported for milled BSA particles. The insight gained from the study of the viscosities and morphologies of suspensions of the model protein BSA will be useful for the design of suspensions of therapeutic proteins such as IgG.

BSA powder or trehalose powder as received was dry milled with a porcelain mortar and pestle separately for several minutes. The milled powder was then sieved through a number 400 mesh and particles smaller than 37 μm were collected. For the mixed milled BSA and trehalose particles, the necessary ratio of BSA to trehalose was then mixed with the mortar and pestle and resieved through the number 400 mesh to preserve the correct particle ratio but retain the smaller than 37 μm particle size. Known weights of powder were suspended in aqueous solutions composed of NMP, PEG 300, and/or ethanol, and sodium chloride or ammonium sulfate salts. The pH was chosen as 4.7, 5.5 or 7.4 with an acetate (pH 4.7 and 5.5) or phosphate (pH 7.4) buffer. Each vial was then shaken by hand to disperse the powder evenly through the suspension. Additional mixing using the tip of the needle was used to ensure uniformity if necessary.

BSA was readily soluble at 5 mg/ml in pH 4.7 150 mM acetate buffer. An aliquot of a 5 mg/ml BSA solution was mixed with an equal volume of a second aqueous solution containing additives for the purpose of determining the degree to which the protein precipitated (either PEG300, NMP or a combination of the two). The precipitation of the protein was classified as highly turbid (HT), lowly turbid (LT, slight turbidity), or no change in turbidity (N). The solutions were all formulated in a pH 4.7 150 mM acetate buffer.

The apparent viscosity of the IgG suspensions was measured as the time to draw 0.25 mL of the suspension into a 25 gauge 1.5" needle attached to a 1 ml tuberculin slip tip syringe. Typical times ranged from 5 to 100 s. Each measurement was made at least 3 times and averaged, while maintaining the suction force by holding the end of the plunger at the 1 ml mark each time. A linear correlation curve for viscosity and time to draw 1 mL (4 times the amount measured) was constructed from measuring liquids of known viscosity (PEG200, PEG 300, PEG 400, water, ethanol, olive oil, and benzyl benzoate). This correlation, as expected from the Hagen-Poiseuille equation, gives an $r^2$ value greater than 0.999 and was reported previously. In most cases the reproducibility in viscosity was within 5%. In our experiments a maximum volume of 25% of the cavity in the syringe was filled with suspension for the uptake. Consequently, the pressure drop was relatively constant. The error introduced by the small change in pressure drop was minimized by using the same plunger position each time and by correlating the data to liquids of known viscosity.

Following the suspension viscosity measurement, the protein suspensions were centrifuged for 20 min at 3000 rpm using a rotating bucket centrifuge rotor (part A-4-62) with a 2 ml centrifuge tube adapter for an Eppendorf Centrifuge (model 5810, Wesbury, N.Y.). The centrifuged samples were photographed and the supernatant was separated by carefully decanting the sample using a needle and syringe. The remaining protein particles were then redispersed in ~15 ml of acetonitrile under gentle bath sonication for 5 min. The dissolution of BSA in acetonitrile was negligible. After redispersion, the protein particle size was then measured for a drop of the sonicated dispersion. The dispersion was diluted to an obscuration of approximately 10% in acetonitrile in a small-volume (11 ml) magnetically stirred cell and the particle size was analyzed by light scattering using the Malvern Instruments Mastersizer S.

After the centrifugation described in the Particle Size Measurement section, the recovered supernatant was then filtered through a 0.22 μm filter and collected. The filtered sample was then diluted to a total volume of 0.7 ml in pH 4.7 150 mM acetate buffer. Three 200 μl aliquots of each sample were then placed on a UV-transparent 96-well plate and imaged at 280 nm using a spectrophotometer. A standard curve of BSA concentrations of 3, 2, 1, 0.5, and 0 mg/ml in the same buffer versus absorbance at 280 nm yielded an $r^2$ value greater than 0.99. The calibration curve was used to regress the soluble concentration values for each sample. If necessary, the sample was subsequently diluted and remeasured till the concentration fell in the range of 0.5-3 mg/ml.

A drop of the aqueous suspension was flash frozen onto frozen aluminum SEM stages maintained at −200° C. with liquid nitrogen. The frozen droplet was lyophilized with 12 hours of primary drying at −40° C. that was followed by a 6 hour ramp to 25° C. and secondary drying for at least 6 hours at 25° C. using a VirTis Advantage Plus XL-70 shelf lyophilizer. The lyophilization produced a dried powder sample on the SEM stage. Dry powder samples of the milled particles were placed on adhesive carbon tape. Each sample was then gold-palladium sputter coated using a Cressington 208 bench top sputter coater to a thickness of 15 nm. Micrographs were then taken using a Zeiss Supra 40 VP scanning electron microscope with an accelerating voltage of 5 kV.

Various additives can be added to decrease the solubility of a protein in aqueous buffer. The turbidimetric studies of solubility in Table 1 indicate that BSA precipitates with either pure PEG and NMP or mixtures thereof even at low protein concentration of 5 mg/ml. Table 2 indicates that PEG is a stronger antisolvent than NMP as a low turbidity suspension (LT) is formed at 30%. Furthermore, mixtures of the two antisolvents can produce synergistic effects on precipitating protein. For example, a 20-20% mixture causes high turbidity whereas 40% NMP does not produce a change in turbidity. Finally for a given total weight % of antisolvent, the turbidity increases as the relative fraction of PEG increases. These experiments indicate that even a dilute 5 mg/ml protein concentration is well above the solubility limit with these antisolvents. Therefore, only a small fraction of the protein will be dissolved with these additives when the overall protein concentration is on the order of 200 mg/ml, a typical concentration for the injectable suspensions.

FIGS. 1A-C are SEM images of particles made by the process of one embodiment of the present invention. FIG. 1A is a SEM image of original milled particles. FIG. 1B is a SEM image of 30% PEG300 suspension at 200 mg/ml flash frozen and lyophilized. FIG. 1C is a SEM image of 25% PEG300 20% ethanol suspension at 350 mg/ml flash frozen and lyophilized.

The morphology of the original milled particles is shown in FIG. 1A. The average particle size was 20 μm. The size was chosen to be small enough to pass through a 25-27 gauge needle with an inside diameter of smaller than 241 μm. A drop of the final suspension was frozen and lyophilized, and SEM was utilized to determine the particle size in the suspensions for two choices of precipitants shown in FIGS. 1B and C. The particle sizes were only modestly larger than that of the original milled particles indicating little growth from particle aggregation or Ostwald ripening. In addition, FIG. 1C shows a slight increase in the amount of smaller sub-1 μm particles. These results indicate that the particle size could essentially be maintained in the suspensions, and that dissolution of the protein was minimal.

The purpose of this section is to describe the mechanisms for protein precipitation and to provide a brief overview of the results for the viscosities for each class of precipitant. To form a suspension of BSA in aqueous media, the media must be designed to prevent a significant fraction of the BSA from dissolving. The solubility of BSA in a pure aqueous buffer at pH of 4.5 is greater than 100 mg/ml. Various additives were introduced to the aqueous buffer media to decrease the solubility including salts, polymers, and water soluble organics.

Table 1 is a table of the precipitation of BSA in PEG and NMP mixtures at 5 mg/ml. (N indicates transparent solution with no change in turbidity versus case without additives, LT indicates low turbidity, HT indicates a high level of turbidity)

| | PEG % | | | | | | | | | | |
|---|---|---|---|---|---|---|---|---|---|---|---|
| NMP % | 0 | 5 | 10 | 15 | 20 | 25 | 30 | 35 | 40 | 45 | 50 |
| 0 | N | N | N | N | N | N | LT | LT | HT | HT | HT |
| 5 | N | N | N | N | N | N | LT | LT | HT | HT | |
| 10 | N | N | N | N | N | LT | HT | HT | HT | | |

-continued

| NMP % | PEG % | | | | | | | | | | |
|---|---|---|---|---|---|---|---|---|---|---|---|
| | 0 | 5 | 10 | 15 | 20 | 25 | 30 | 35 | 40 | 45 | 50 |
| 15 | N | N | N | N | LT | HT | HT | HT | | | |
| 20 | N | N | N | N | HT | HT | HT | | | | |
| 25 | N | N | N | LT | HT | HT | | | | | |
| 30 | N | N | N | HT | HT | | | | | | |
| 35 | N | N | HT | HT | | | | | | | |
| 40 | N | LT | HT | | | | | | | | |
| 45 | N | HT | | | | | | | | | |
| 50 | N | | | | | | | | | | |

The mechanisms by which the solubility is lowered is given for each type of precipitant in Table 2. Formation of an opaque white concentrated suspension at 200 mg/ml was possible for all three various additive groups as seen in Table 1. Table 2 is a comparison of different additives to lower solubility of a protein, suggested mechanism for the decrease in solubility and the suspension viscosity measured at 200 mg/ml in 150 mM pH 4.7 acetate buffer plus each additive.

| Additive | Mechanism to lower protein solubility | Example of Suspension Viscosity for 200 mg/ml milled BSA |
|---|---|---|
| Salts | Competition for waters of hydration<br>Ion binding changing protein-protein interaction<br>Decrease in electrostatic repulsion with a decrease in the double layer thickness | 3 cP for 1.5M $(NH_4)_2SO_4$ |
| Polymers | Preferentially Preferential exclusion from protein surface leading to depletion attraction<br>Lower solvent dielectric constant | 18 cP 30% PEG300 |
| Water Soluble Organics | Lower solvent dielectric constant<br>Exclusion of solvent from protein surface produces excluded volume effects | 10 cP for 35% n-methyl-2-pyrrolidone (NMP) |

A summary of select viscosity results measured with a 25 g 1.5" needle, which are described in greater detail below, is also presented in Table 2. An extremely low viscosity of 3 cp was obtained with 1.5M $(NH_4)_2SO_4$. The values were also quite low for the other PEG and NMP antisolvents. All three of these examples are well within the limits of what would be considered easily syringeable, since it would take less than 20 seconds to expel 1 ml from a 26 g needle. These results will be examined in much greater detail below in context of the morphologies of the particles and of the suspensions and for a much wider range of conditions.

Figure 2:
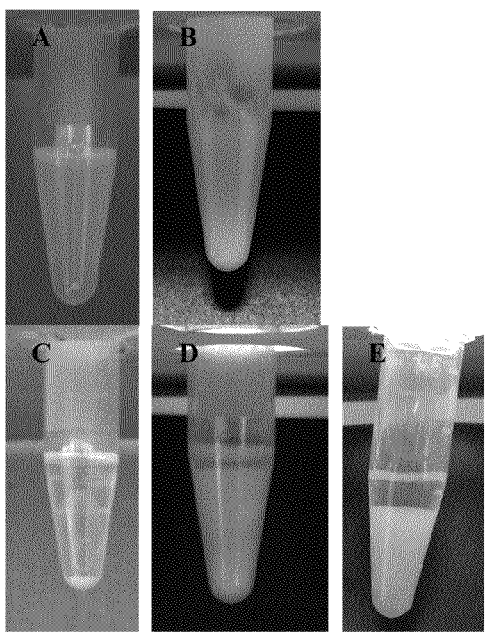
FIGS. 2A-2E are images of suspensions before (FIGS. 2A and B) and after (FIGS. 2C-E) centrifugation (20 min at 3000 rpm) from left to right 1.5M Ammonium Sulfate (a and c), 30% PEG300 (b and d), 35% NMP (e) all in 150 mM pH 4.7 acetate buffer with added NaCl to 154 mM ionic strength.

FIGS. 2A-2E are images of suspensions before (FIGS. 2A and B) and after (FIGS. 2C-E) centrifugation (20 min at 3000 rpm) from left to right 1.5M Ammonium Sulfate (a and c), 30% PEG300 (b and d), 35% NMP (e) all in 150 mM pH 4.7 acetate buffer with added NaCl to 154 mM ionic strength. As shown in FIG. 2, the various solubility-decreasing additives produced different amounts of suspended large particles. The relative quantity of suspended particles is evident qualitatively from the turbidity of the initial suspension. An opaque white suspension was formed for 30% PEG300 and 35% NMP as shown in FIGS. 2B and 2E suggesting a large amount of suspended particles relative to dissolved protein. This observation is confirmed more quantitatively by the volume fraction of the precipitant after 20 minutes of centrifugation at 3000 rpm, indicating very little of the protein was soluble. This force is sufficient to settle out all particles greater than ~400 nm. These results support the direct observation of micron-sized protein particles in the suspensions by cryo-SEM in FIG. 1C. For 1.5M ammonium sulfate salt as an additive, the original suspension was only translucent indicating a much smaller degree of precipitation. After centrifugation, only a small volume of precipitate was present (FIGS. 2A and C) consistent with the observation of relatively low turbidity in the original suspension. The degree of precipitation as characterized by the turbidity of the initial suspension and the volume fraction of precipitant after centrifugation will be an important factor for understanding the viscosity behavior of the suspensions.

As shown in Table 2, an aqueous suspension with 30% PEG300 gives an apparent viscosity of 18 cP for 200 mg/ml BSA. This low viscosity may be examined in terms of the presence of protein particles relative to dissolved protein in solution. As has been demonstrated previously, with the addition of 30% PEG300, the solubility of BSA is reduced from approximate 6 mg/ml at 25%, to 1 mg/ml. This large decrease in solubility was verified in Table 1 by the increase in turbidity for a level of precipitant between 25% and 30% (by volume) PEG300 at a protein concentration of 5 mg/ml.

Suspensions of the pure milled BSA particles were formed for PEG300 levels between 30 and 50% by volume. Two key factors influence the viscosity of the suspension at a given volume fraction of protein: the initial viscosity of the solution without protein and the intrinsic viscosity with protein present. Table 3 shows the Intrinsic Viscosity data of suspensions to compare effects of electroviscous and hydration, all samples at pH 4.7 acetate 150 mM ionic strength buffer (unless indicated otherwise). For intrinsic viscosity measurement, $\phi_{max}$ assumed to be 0.64. (NMP—N-methyl-2-pyrrolidone, ND—not determined) The average particle diameter was determined by static light scattering was 20 µm.

| Solvent system | Solution Viscosity (cP) | Suspension Apparent Viscosity at 250 mg/ml BSA (cP) | Intrinsic Viscosity [η] | Average Particle Diameter (µm) | Soluble Concentration (mg/ml) |
|---|---|---|---|---|---|
| 30% PEG300 | 2.6 | 56 | 11.4 | 9.6 | ND |
| 40% PEG300 | 4.6 | 85 | 9.6 | 17.4 | 2.0 |
| 50% PEG300 | 6.6 | 49 | 7.9 | 18.5 | 2.1 |

-continued

| Solvent system | Solution Viscosity (cP) | Suspension Apparent Viscosity at 250 mg/ml BSA (cP) | Intrinsic Viscosity [η] | Average Particle Diameter (μm) | Soluble Concentration (mg/ml) |
|---|---|---|---|---|---|
| pH 5.5 50% PEG300 | 6.2 | 47 | 8.4 | 18.4 | ND |
| pH 7.4 50% PEG300 | 6.0 | 57 | 9.0 | ND | ND |
| 40% PEG300 and 10% NMP | 5.1 | 22 | 6.0 | 20.2 | 2.9 |
| 35% PEG300 and 15% NMP | 4.8 | 20 | 5.9 | 19.1 | 2.9 |
| 25% PEG300 and 20% NMP | 3.6 | 18 | 6.5 | 19.5 | 2.3 |
| 25% PEG300 and 20% Ethanol | 3.3 | 14 | 5.8 | 7.4 | 4.8 |

As shown in Table 3, the solution viscosity (without protein) increases from 2.6 for a 30% PEG300 solution to 6.6 for a 50% PEG300 solution. At the same time however, the intrinsic viscosity decreased from 11.4 to 7.9. Consequently the overall suspension viscosity went down about 10%, a value twice that of the experimental uncertainty. Interestingly, the viscosity was higher at 40% PEG than 30%, as the intrinsic viscosity did not decrease enough to compensate for the higher solvent viscosity (without protein). Thus, the amount of precipitant may be optimized to balance its effect on the initial viscosity of the solution without protein versus the intrinsic viscosity of the protein suspension.

Figure 3:
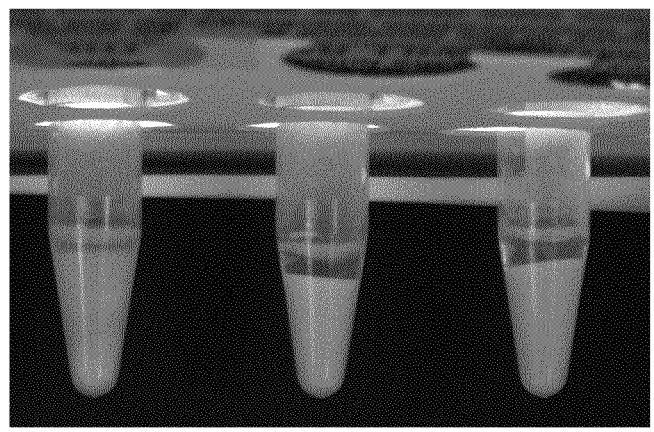
FIG. 3 is an image of aqueous PEG 300 suspensions after 20 min of centrifugation at 3000 g. From left to right 30% PEG300, 40% PEG300, and 50% PEG 300 all in 150 mM pH 4.7 acetate buffer with added NaCl to 154 mM ionic strength.

FIG. 3 is an image of aqueous PEG 300 suspensions after 20 min of centrifugation at 3000 g. From left to right 30% PEG300, 40% PEG300, and 50% PEG 300 all in 150 mM pH 4.7 acetate buffer with added NaCl to 154 mM ionic strength. All 3 of the PEG-based suspensions after 20 min of centrifugation at 3000 g exhibited a high degree of large settled particles (FIG. 3). However, for the 30% PEG300 suspension, the supernatant appears slightly turbid, indicating the presence of small suspended nanoparticles. Thus, a soluble concentration was not determined for this case. The soluble concentration for the 40 and 50% PEG300 suspensions was between 2.0-2.1 mg/ml indicating that 99% of the particles at 200 mg/ml were suspended (Table 3). The average particle diameters for the 40 and 50% PEG300 suspensions were both near the original 20 μm value for the milled particles, as shown in table 3. However, for the 30% PEG300 suspension, the average particle diameter decreased to ~10 μm consistent with greater dissolution on the basis of the turbidity of the supernatant. This decrease in size is consistent with the observation by SEM in FIG. 1. These smaller particles with higher surface area, and dissolved protein contributed to the higher intrinsic viscosity in Table 3.

For the 30% PEG300 formulation, additional apparent suspension viscosities were measured at higher ionic strengths, shown in Table 4. As the ionic strength of the solution increased, the viscosity decreased from 56 to 19. The decrease in the electroviscous effects with an increase in ionic strength and a decrease in the Debye length contributes significantly to the decrease in intrinsic viscosity and thus the suspension viscosity.

| Ionic strength (mM) | Apparent Viscosity (cP) |
|---|---|
| 150 | 56 |
| 300 | 23 |
| 500 | 19 |

To change the charge of the protein and the solubility, the solution pH was increased from the pI of BSA (4.7) to a pH of 5.5, while maintaining the acetate ion as the buffer. In addition, a phosphate buffer ion was used as opposed to acetate buffer ion to raise the pH of 7.4. Since the solubility of a protein increases as the pH moves away from the pI, the 50% PEG300 additive was included in the media to ensure a low solubility of BSA.

Figure 4:
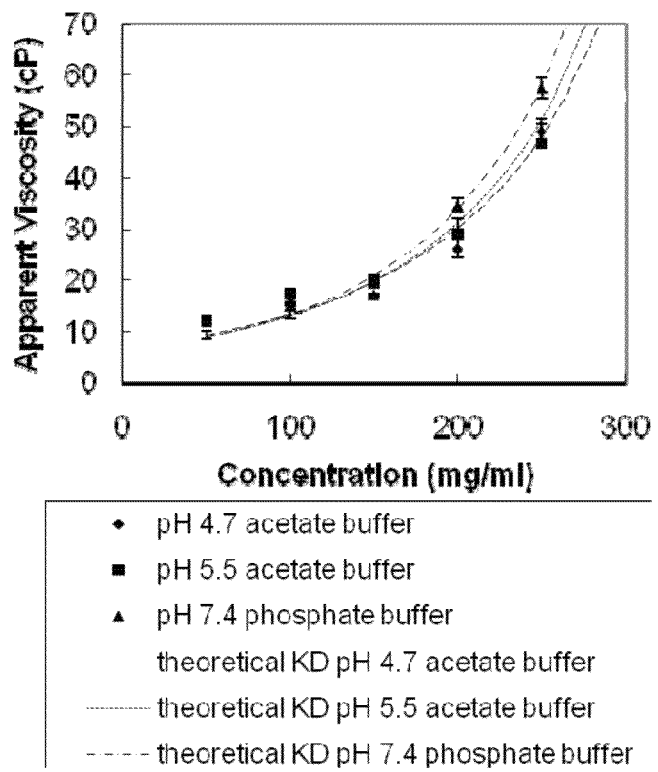
FIG. 4 is a graph of the apparent viscosity of aqueous suspensions at various pHs all with 50% PEG 300 and added NaCl to 154 mM ionic strength.

FIG. 4 is a graph of the apparent viscosity of aqueous suspensions at various pHs all with 50% PEG 300 and added NaCl to 154 mM ionic strength. As shown in FIG. 4, neither the buffer ion nor the pH made a significant change in the apparent suspension viscosity at any concentration. The solution viscosities for the varying pHs with 50% PEG300 varied only slightly from 6.0-6.6. Since the apparent viscosities for all cases at all concentrations were similar, the calculated intrinsic viscosities increased only slightly from 7.9 to 9.0 for the increase in pH. The theoretical curves in FIG. 4 were determined by regressing the intrinsic viscosity (Table 3) with the Krieger-Dougherty equation.

Figure 5:
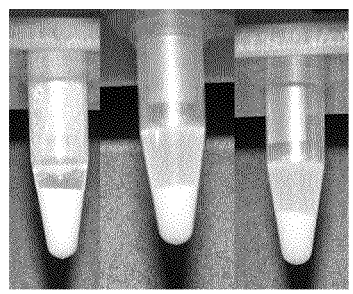
FIG. 5 is an image of aqueous 50% PEG 300 suspensions after 20 min. of centrifugation at 3000 g. From left to right pH 4.7 acetate buffer, pH 5.5 acetate buffer, and pH 7.4 acetate buffer.

FIG. 5 is an image of aqueous 50% PEG 300 suspensions after 20 min. of centrifugation at 3000 g. From left to right pH 4.7 acetate buffer, pH 5.5 acetate buffer, and pH 7.4 acetate buffer. As shown in FIG. 5, the supernatant is still turbid for both the pH 5.5 and pH 7.4 samples after centrifugation. As a result, the soluble concentration could not be determined and the average particle size could only be determined for the pH 5.5 sample. While the average particle diameter at pH 5.5 is very similar to the average particle diameter at pH 4.7, the increase in turbidity of the supernatant indicates the presence of some additional smaller nanoparticles, not present in the pH 4.7 samples.

FIG. 6 is a graph of the apparent viscosity of aqueous suspensions with PEG 300 and organic additives in 150 mM pH 4.7 acetate buffer with added NaCl to 154 mM ionic strength. As shown in FIG. 6, upon addition of 10-20% of an organic additive to at least 25% PEG300, the apparent viscosity of the suspension remained below 50 cP even for extremely high BSA concentrations greater than 300 mg/ml. Furthermore, as shown in table 3, all of these PEG300 plus organic suspensions reduce apparent viscosities to a range of 14-22 cP at a BSA concentration of 250 mg/ml. This viscosity range is approximately the same as for the higher ionic strength samples (300 and 500 mM) discussed above (Table 4). These PEG300-organic samples gave the lowest intrinsic viscosity values (5.8-6.5) measured in this study (Table 3). All three samples with 10-20% NMP added, gave particle diameters that were very close to the original 20 μm milled particles. In addition, the soluble concentration for all three NMP samples was between 2.3-2.9 mg/ml, indicating the suspension of greater than 99% of the BSA added at the 300 mg/ml level (Table 3). The sample with 20% ethanol added had the lowest solution viscosity, giving the lowest suspension viscosity at 250 mg/ml of 14 cP (Table 3). The slightly higher soluble concentration of 4.8 mg/ml indicated that greater than 98% of the BSA added was suspended. However, this slight decrease in percent suspended was sufficient to decrease the average particle diameter to 7.4 μm. The slight decrease in particle size could be seen in the SEM imaged.

All of the above samples contained milled model protein, BSA, without a sugar lyoprotectant that can help stabilize a therapeutic protein at the molecular level against monomer aggregation. BSA is a fairly stable protein and thus the molecular stability was not considered in this study. However, milling can generate instabilities for many therapeutic proteins. {Maa} On the other hand, freezing and lyophilizing of protein particles has been shown to produce molecularly stable protein particles even for submicron sizes. A very common lyoprotectant is trehalose.

FIGS. 7A and 7B are graphs that show the apparent viscosities of milled BSA and trehalose at various ratios in 150 mM pH 4.7 acetate buffer along with the theoretical viscosity as calculated from the Krieger-Dougherty equation using the [η] of the pure milled particles in a) 25% PEG 300 20% Ethanol and b) 35% PEG 300 and 15% NMP. FIG. 7 shows images of data of protein and BSA particles at ratios from 1:0.1 to 1:1 by weight BSA to trehalose. At all points, the higher ratios of trehalose to BSA increase monotonically the viscosity of a suspension formed in either 25% PEG300 20% ethanol or 35% PEG300 and 15% NMP. Even though the trehalose will be soluble in the aqueous solvents with the additives, it will still contribute additional excluded volume that is unavailable either to the solvent or the undissolved particles. This excluded volume will therefore decrease the highest loading of particles possible to maintain a given viscosity. The theoretical lines in FIG. 7 were calculated using the same intrinsic viscosity for the respective suspensions without trehalose and assuming a maximum volume fraction of 0.64.

Antibody therapeutics currently constitute a market size of $15 billion dollars annually, addressing needs in anti-cancer, anti-infective and anti-inflammatory diseases. As large protein molecules, these currently require direct injection (intravenous or subcutaneous) for delivery. Since the required doses are quite large and frequently administered, this poses a considerable obstacle for drug delivery: to achieve subcutaneous delivery with a small bore syringe, the antibody must be formulated in a high concentration (>100 mg/ml), low volume (<1.5 ml), low viscosity (<100 cP) format. These specifications have been very difficult to achieve with traditional solution formulations (in a phosphate buffer containing trehalose) but suspensions of lyophilized antibody in aqueous solvents containing salts and precipitants to prevent dissolution represent a possible option. We have previously demonstrated the success of this approach with a model protein, BSA and here present an extension of the technology to polyclonal antibodies. Here we present for the first time, evidence that immunoglublins can be prepared as aqueous suspensions in concentrations up to 200 mg/ml, with low viscosity and no aggregation (96% monomeric protein).

IgG purified from sheep serum (Product No. I5131) was purchased from Sigma-Aldrich, Inc. α-α trehalose, polyethylene glycol with an average molecular weight of 300 (PEG 300), ammonium sulfate, USP grade ethanol, and n-methyl 2-pyrrolidone (NMP) were purchased from FisherChemicals.

After dissolving a known amount of the IgG in an appropriate amount of a 20 mM pH 5.5 histidine buffer with α-α trehalose, samples were slow frozen on a pre-cooled lyophilizer shelf at −40° C. The samples were then lyophilized for 12 hours at −40° C. at 100 mTorr, followed by a 6 hour ramp to 25° C. at 50 mTorr, and maintained for secondary drying at 25° C. at 50 mTorr for at least an additional 6 hours. 1 mg of powder was then weighed out and reconstituted at 1 mg/ml in 200 mM pH 7.0 phosphate buffer for stability analysis by size exclusion chromatography as described below.

An aliquot of a 5 mg/ml IgG solution was mixed with an equal volume of a second aqueous solution containing additives for the purpose of lowering the protein solubility. The precipitation of the protein was characterized by an increase in turbidity of the solution after 24 hours at a wavelength of 350 nm. The solutions were all formulated in a pH 6.4 20 mM histidine buffer with added PEG300 and NMP. The turbidity of a 100 μl aliquot of the final formulation was measured on a UV-transparent 96-well plate using a spectrophotometer.

Aqueous-based solvent mixtures, without protein, containing varying volume percents of NMP, PEG 300, and ethanol and various molarities of sodium chloride or ammonium sulfate salts were mixed to form uniform transparent solutions. These solutions were buffered at varying ionic strengths usings either a histidine or phosphate buffer at pH 6.4 (the isoelectric point of sheep IgG). Samples of the protein were then compacted into 0.1 ml conical vials such that the powder weight was within 5% of the desired weight. The powder weight depended upon the final protein concentration and the excipient/protein ratio. A measured amount of the prepared aqueous-based solvent mixture was added to the conical vial to form a suspension with a total volume of 0.1 ml. The mixture was stirred the tip of a needle to remove air pockets and to form the suspension with sufficient uniformity. Sonication was not used, nor was it needed. A drop of the uniform suspension was then placed on a microscope slide to image the suspension and 10 μl of the suspension was diluted to 1 mg/ml in a 200 mM pH 7.0 phosphate buffer to measure the protein monomer fraction by size exclusion chromatography as specified below.

The apparent viscosity of the IgG suspensions was measured as the time to draw 50 μl of the suspension into a 25 gauge 1.5" needle attached to a 1 ml tuberculin slip tip syringe. A conically shaped vial was used to minimize the sample volume given the cost of the protein. Videos of the conical vial containing the suspension were taken and the time to draw from a height 0.4" from the bottom of the cone to a height 0.1" from the bottom of the cone was measured using Image J software. The uncertainty in the height was on the order of 1%. The time was measured to within 0.05 seconds as the video was converted to an image stack with 20 images per second. Each measurement was made at least 3 times and averaged, while maintaining the suction force constant for each measurement by holding the end of the plunger at the 1 ml mark each time. In most cases the reproducibility in viscosity was 10%. Previous work with suspensions of model proteins found that the time to draw up a specified amount of the sample in a syringe was correlated linearly to viscosity. A maximum volume of 10% of the cavity in the syringe was filled with suspension for the uptake. Consequently, the pressure was essentially constant and the viscosity may be obtained from the Poiseulle equation. In this case, using standard solutions with various viscosities (pure DI water, ethanol, PEG 200, PEG300, PEG400 and benzyl benzoate) gave a linear correlation between the time to draw 0.05 ml from the conical vial to the viscosity with an $r^2$ value greater than 0.99.

Samples for scanning electron microscopy (SEM) of the dry powders after lyophilization were placed on adhesive carbon tape. Each sample was then gold-palladium sputter coated using a Cressington 208 bench top sputter coater to a thickness of 15 nm. Micrographs were then taken using a Zeiss Supra 40 VP scanning electron microscope with an accelerating voltage of 5 kV. Optical microscope images of a drop of the final suspensions on a glass microscope slide were taken using an MTI CCD 72 (Dage-MTI, Michigan City, Ind.) camera attached to a Nikon Optiphot2-Pol (Nikon Instruments Inc. Melville, N.Y.) microscope.

Percent monomer of the initial solution, reconstituted powder and final diluted suspension was analyzed by using Tosoh Biosciences G3000SWXL size exclusion column followed by a G2000SWXL size exclusion column attached to Waters Breeze HPLC system containing a model 717 plus autosampler, 2487 dual wavelength detector, and 1525 binary pump (Waters Corporation, Milford, Mass.). The prepared samples, reconstituted or diluted to ~1 mg/ml in 200 mM pH 7.0 phosphate buffer were filtered through a 0.22 µm Millex-GV filter to remove large aggregates prior to analysis. The mobile phase consisted of a pH 7.0 200 mM phosphate buffer and 50 mM sodium chloride at a flow rate of 0.7 ml/min. The detection wavelength was 214 nm. An injection volume of 20 µl of the ~1 mg/ml prepared sample was used. The monomer eluted at approximately 21.5 minutes, with the higher molecular weight aggregates eluting in the last few minutes before this, depending on their size.

Figure 8:
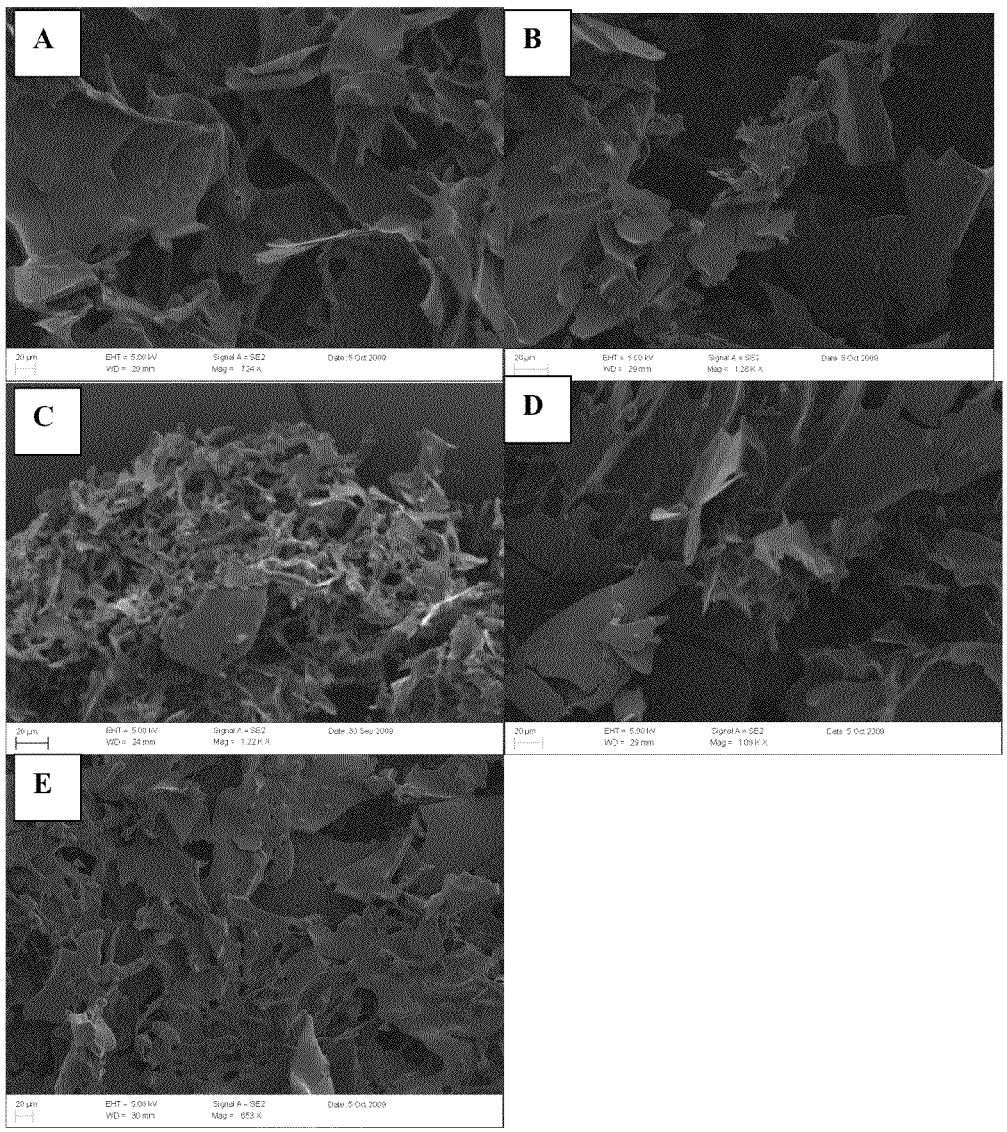
FIGS. 8A-8E are SEM images of various frozen powders of IgG.

FIGS. 8A-8E are SEM images of various frozen powders of IgG. FIG. 8A is a SEM image of 40 mg/ml IgG frozen at a 1:1 IgG to trehalose ratio. FIG. 8B is a SEM image of 55 mg/ml IgG frozen at a 1:0.5 IgG to trehalose ratio. FIG. 8C is a SEM image of 25 mg/ml IgG frozen at a 1:0.5 IgG to trehalose ratio. FIG. 8D is a SEM image of 40 mg/ml IgG no trehalose. FIG. 8E is a SEM image of 20 mg/ml IgG at a 1:1 IgG to trehalose ratio. Large micron-sized particles of IgG stabilized by α-α trehalose were made by lyophilization using a 1:1, 0.5:1, 0.25:1, or 0:1 ratio of trehalose to IgG in a 20 mM pH 5.5 histidine buffer at various initial concentrations between 20-80 mg/ml of IgG. SEM micrographs of the final dried powder show large 10-100 µm particles with relatively few fine particles (on the order of hundreds of nanometers) for the particles frozen at higher concentrations (40 to 80 mg/ml) for each trehalose to IgG ratio (FIGS. 8A and 8B), including the case with no trehalose (FIG. 8D). The large particles are in contrast to the smaller web-like morphology visible for the protein frozen at lower concentrations, 20 and 25 mg/ml IgG, with high ratios of IgG to trehalose, 1:1 and 1:0.5 respectively (FIGS. 8C and 8E). During freezing, a higher concentration of protein leads to greater growth and thus larger final particles.

The relative stability from SEC was defined as the difference in percent area of the monomer peak after reconstitution of the dry powder in pH 7.0 phosphate buffer relative to the initial powder diluted in the same pH 7.0 phosphate buffer. This relative stability was at least 98.6% and often higher. The stability was high even for the 40 mg/ml IgG powder frozen without any trehalose, indicating cryoprotectant is not needed to achieve high stabilities as measured by this technique. However this value of 98.6 is lower than that of all of the other examples in the table that included trehalose. Thus, a cryoprotectant can be beneficial for increasing the stability, and trehaolse was included.

Precipitation of 5 mg/ml IgG solution with various additives. Various additives can be added to decrease the solubility of the IgG as described in detail above. We have confirmed this by observation of precipitation in a high molarity (1.5M) ammonium sulfate solution at an IgG concentration of 5 mg/ml (optical density not determined).

Figure 9:
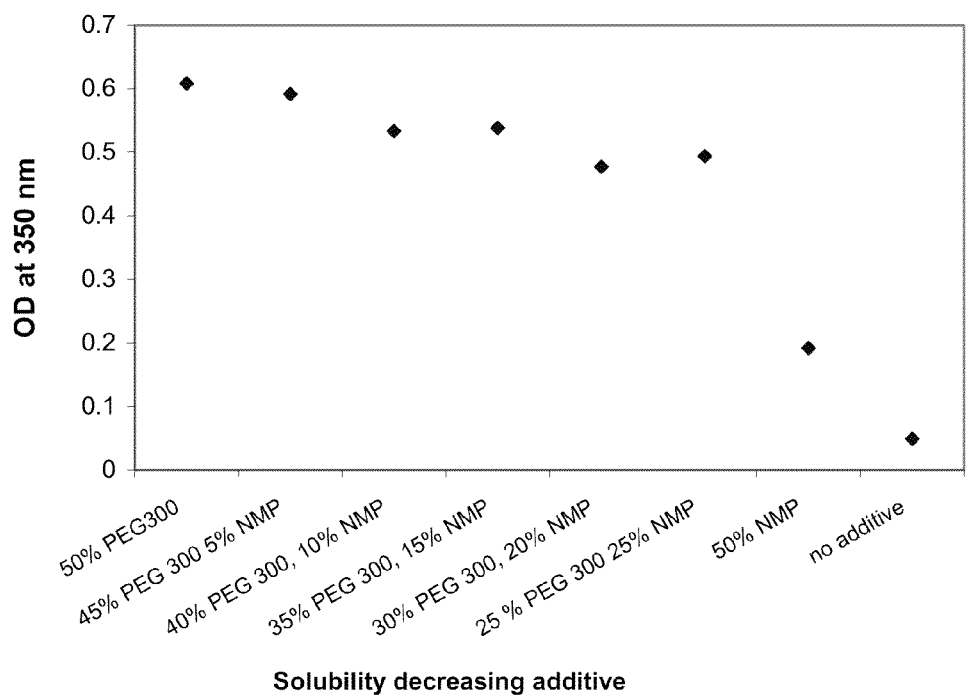
FIG. 9 is a graph of the optical density of the IgG with various additives totaling 50% of the solvent by volume to decrease the solubility of the IgG as measured at 350 nm. The right hand side has the absorbance of the 5 mg/ml concentration of IgG in the pH 6.4 20 mM histidine buffer with no additional additive.
Figure 10:
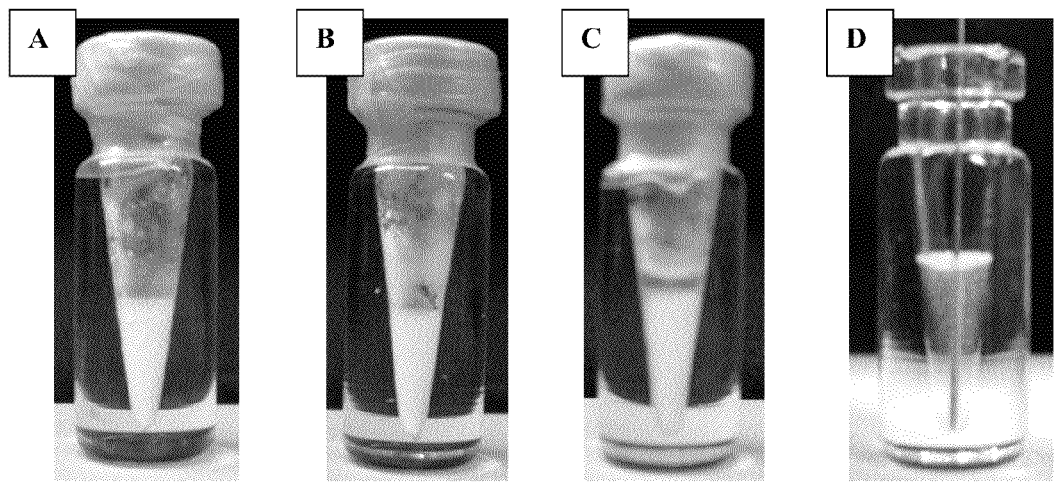
FIG. 10A-10D are images of various suspensions of IgG.

FIG. 9 is a graph of the optical density of the IgG with various additives totaling 50% of the solvent by volume to decrease the solubility of the IgG as measured at 350 nm. The right hand side has the absorbance of the 5 mg/ml concentration of IgG in the pH 6.4 20 mM histidine buffer with no additional additive. As shown in FIG. 9, at a concentration of 5 mg/ml IgG, the absorbance at 350 nm increases from ~0.05 for the pure protein solution at pH 6.4 to ~0.6 for a 50% volume solution of PEG300 at pH 6.4 (FIG. 9). For the IgG at this concentration in a 50% volume solution of NMP at pH 6.4, the absorbance at 350 nm was significantly lower at ~0.2 than for the case of 50% PEG300 (FIG. 9). The absorbance at 350 nm of mixed samples of PEG300 and NMP totally 50% by volume of the solvent, with at least 25% PEG300 were similar. The absorbance decreased slightly as the % NMP increased from ~0.6 to 0.5 for a 25% PEG300 and 25% NMP mixed solution. However, a much lower absorbance of ~0.2 was observed for a 50% NMP solution, without any PEG. These experiments indicate that proteins precipitate with these additives even at low protein concentration of 5 mg/ml. Therefore, only a small fraction of the protein will be dissolved with these additives when the overall protein concentration is on the order of 200 mg/ml, a typical concentration for the injectable suspensions.

Figure 11:
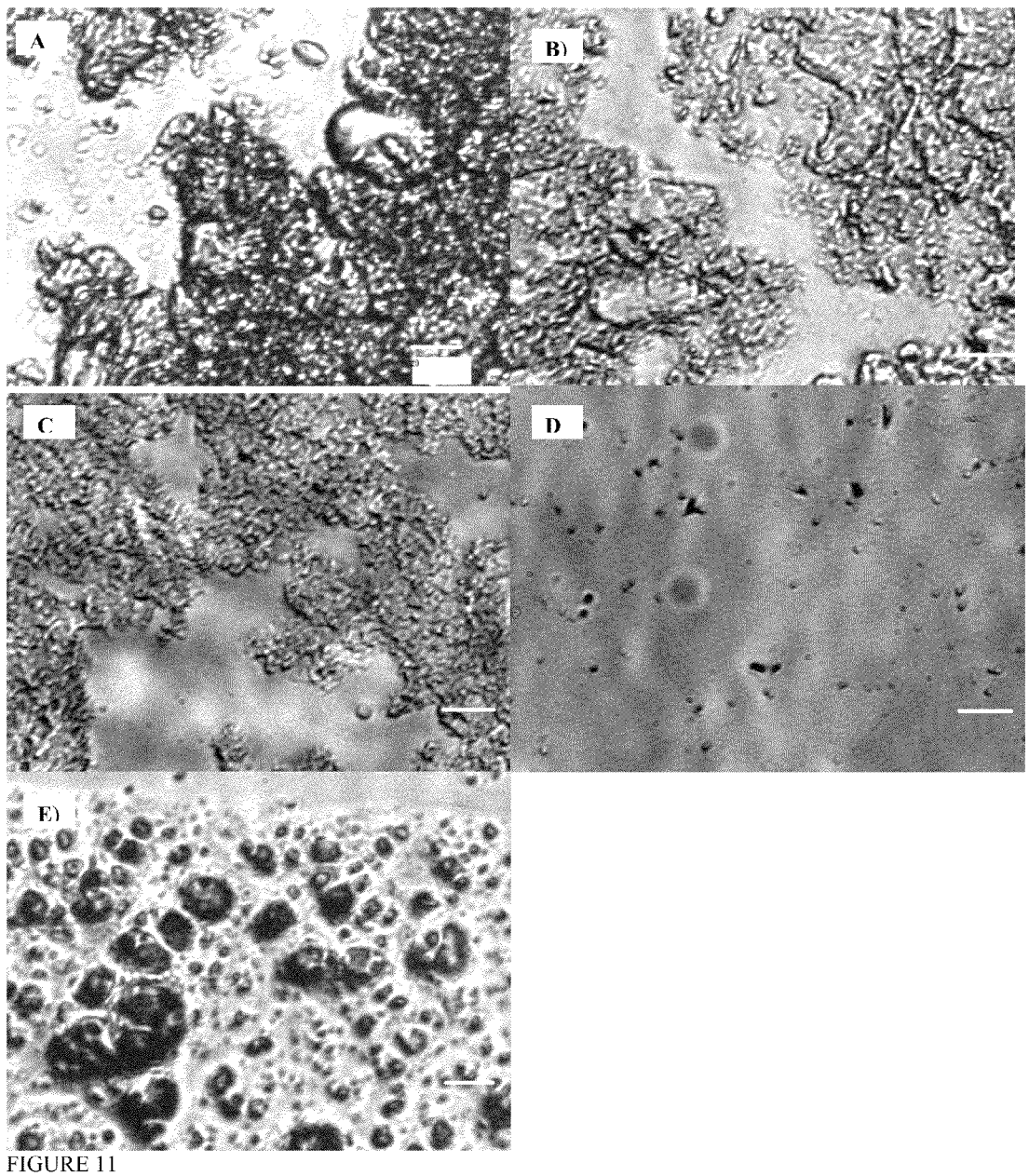
FIG. 11A-11E are microscope images of various suspensions of IgG.

Suspension morphology as a function of particle size. In addition to the ratio of trehalose to protein in the lyophilized particles, the size and surface area of the particles, will vary the morphology and viscosity (syringeability) of the suspension. The optimum particle size contains particles small enough to flow up the 25 gauge needle however large enough to minimize the detrimental effects of hydration and electroviscous forces on the viscosity. Furthermore, a decrease in the surface area of the particles may decrease denaturation and aggregation of the protein.

FIG. 10A-10D are images of various suspensions of IgG. A) 200 mg/ml IgG suspension made of 55 mg/ml IgG 1:0.5 IgG to trehalose ratio particles in 20 mM pH 6.4 histidine buffer with 1.5M added ammonium sulfate salt. B) 200 mg/ml IgG suspension made of 55 mg/ml IgG 1:0.5 IgG to trehalose ratio particles in 50 mM pH 6.4 phosphate buffer with 50% PEG300. C) 200 mg/ml IgG suspension made of 55 mg/ml IgG 1:0.5 IgG to trehalose ratio particles in 50 mM pH 6.4 phosphate buffer with 35% PEG300 and 15% NMP by volume after 24 hours D) 200 mg/ml IgG suspension made of 20 mg/ml IgG with 1:1 IgG to trehalose ratio particles in 50 mM pH 6.4 phosphate buffer with 35% PEG300 and 15% NMP by volume.

In FIG. 10A and FIG. 10B, a concentrated suspension is shown for two different additives and an IgG concentration of 200 mg/mL initially after forming the suspension. The suspensions were white and opaque. The path length was approximately 0.5 cm at the mid-point of the cone. The particles in a droplet of the suspension were further characterized with optical microscopy in FIG. 4. Micron-sized particles are present in the range of a few microns to 10 micron, consistent with the dry initial particles from the SEMs in FIG. 8. FIG. 10C illustrates a typical example of a small degree of settling of these suspensions in FIG. 10A and FIG. 10B after 24 hours. In FIG. 10D, the initial concentration for lyophilization was much lower, 20 mg/ml, and the particles were much smaller as evident in SEM and by optical microscopy of the suspension. These smaller particles did not scatter light as strongly, and the suspension appeared translucent, instead of white and opaque.

FIG. 11A-11E are microscope images of various suspensions of IgG. FIG. 11A is an image of 200 mg/ml IgG suspension made of 55 mg/ml IgG 1:0.5 IgG to trehalose ratio particles in 20 mM pH 6.4 histidine buffer with 1.5M added ammonium sulfate salt. FIG. 11B is an image of 200 mg/ml IgG suspension made of 55 mg/ml IgG 1:0.5 IgG to trehalose ratio particles in 50 mM pH 6.4 phosphate buffer 50% PEG300. FIG. 11C is an image of 200 mg/ml IgG suspension made of 55 mg/ml IgG 1:0.5 IgG to trehalose ratio particles in 50 mM pH 6.4 phosphate buffer 35% PEG300 15% NMP. FIG. 11D is an image of 200 mg/ml IgG suspension made of 20 mg/ml IgG 1:1 IgG to trehalose ratio particles in 50 mM pH 6.4 phosphate buffer 35% PEG300 15% NMP. FIG. 11E is an image of 200 mg/ml IgG suspension made of 80 mg/ml IgG 1:1 IgG to trehalose ratio particles in 50 mM pH 6.4 phosphate buffer 35% PEG300 15% NMP. Table 5 illustrates size was caused by the high starting concentration during lyophilization. They were suspended in the 35% PEG300 15% NMP solvent described in Table 2. The particle size reached >50 micron, and therefore, the particles did not flow through a 25 gauge syringe. In contrast, all of the smaller particles in FIG. 11 were syringeable.

Table 8 illustrates IgG suspensions in various buffers with various additives screened for their viscosity and % monomer of the original sample present. (ND—not determined; EtOH—ethanol, NMP—N-methyl-2-pyrrolidone).

| Suspension Additive | Suspension Buffer | IgG Suspension Concentration (mg/ml) | Frozen IgG Concentraion (mg/ml) | Trehalose: IgG (wt.) ratio in frozen powder | Viscosity (cP) | SEC (% monomer of dry powder) |
|---|---|---|---|---|---|---|
| 50% PEG300 | 20 mM pH 7.4 histidine buffer | 100 | 40 | 1:1 | 46 | ND |
| 50% PEG300 | 50 mM pH 6.4 phosphate buffer | 170 | 55 | 0.5:1 | 72 | 102.0 |
| 50% PEG300 90 mM $(NH_4)_2SO_4$ | 50 mM pH 6.4 phosphate buffer | 200 | 55 | 0.5:1 | 78 | ND |
| 40% PEG300 10% EtOH | 40 mM pH 7.4 histidine buffer | 100 | 40 | 1:1 | 43 | ND |
| 35% PEG300 15% EtOH | 50 mM pH 6.4 phosphate buffer | 200 | 55 | 0.5:1 | 92 | 93.6 |
| 30% NMP 10% PEG300 | 20 mM pH 7.4 histidine buffer | 200 | 40 | 1:1 | 71 | ND |
| 1.5M $(NH_4)_2SO_4$ | 20 mM pH 6.4 histidine buffer | 200 | 55 | 0.5:1 | 12 | 97.8 |
| 1.5M $(NH_4)_2SO_4$ | 20 mM pH 6.4 histidine buffer | 300 | 55 | 0.5:1 | 99 | 101.2 |

IgG lyophilized powders made at various protein concentrations and trehalose ratios in a 20 mM pH 5.5 histidine buffer, characterized for the stability of the dry powder by size-exclusion HPLC.

| Protein concentration (mg/ml) | Trehalose:IgG (wt.) ratio | SEC (% monomer of original solution) |
|---|---|---|
| 20 | 1:1 | 99.1 |
| 25 | 0.5:1 | 100.1 |
| 40 | 0 | 98.6 |
| 40 | 1:1 | 101.6 |
| 55 | 0.5:1 | 99.8 |
| 65 | 0.25:1 | 99.9 |
| 80 | 0 | 100.1 |

Table 6 illustrates 200 mg/ml IgG suspensions in a solvent containing 35% PEG300, 15% N-methyl-2-pyrrolidone (NMP) by volume added to a 50 mM pH 6.4 phosphate buffer. (ND—not determined; NM—immeasurable).

| Frozen IgG Concentration (mg/ml) | Trehalose:IgG (wt.) ratio in frozen powder | Viscosity (cP) | SEC (% monomer of dry powder) |
|---|---|---|---|
| 20 mg/ml IgG | 1:1 | ND | 102.6 |
| 40 mg/ml IgG | 0 | 52 | 79.7 |
| 40 mg/ml IgG | 1:1 | 194 | 98.0 |
| 55 mg/ml IgG | 0.5:1 | 104 | 97.1 |
| 65 mg/ml IgG | 0.25:1 | 144 | 86.9 |
| 80 mg/ml IgG | 0 | NM | ND |

The largest particles were formed with pure IgG particles frozen at 80 mg/ml as shown in FIG. 11E. The large particle size was caused by the high starting concentration during lyophilization.

Viscosities less than 100 cP are sufficient for syingeability through a 25 gauge 1.5" syringe. Syringeable viscosities were obtained for suspensions at concentrations up to 200 mg/ml IgG (Tables 6-8). The addition of a cryoprotectant, such as trehalose, as seen previously for BSA powders {Miller aqueous BSA}, will increase the viscosity of a suspension (Table 6). This increase is caused primarily by the excluded volume occupied by the cryoprotectant. For example, in Table 6, the 200 mg/ml IgG suspension, with no trehalose has a viscosity of 52 cP as opposed to 104 for a 0.5:1 ratio of trehalose to IgG. The addition of trehalose increases the total solute (trehalose plus IgG) concentration to 300 mg/ml. Further increasing the total solute concentration to 400 mg/ml by increasing to a 1:1 ratio of IgG to trehalose, raises the viscosity further to 194 cP. Thus, the potential need for a cryoprotectant to form stable protein molecules must be balanced against the increase in viscosity due to the excluded volume of a cryoprotectant. To examine the relationship between the precipitation seen in the solubility study above and the viscosity of the suspension a series of tests were run using the 55 mg/ml IgG 0.5:1 trehalose:IgG particles. For the additive conditions in the first three entries in Table 7, high ODs were obtained at even the low protein concentration of 5 mg/ml in the solubility determinations in FIG. 9. The vials for these 150 mg/ml protein suspensions were white opaque as in FIG. 3. These samples had measurable viscosities between 57 and 98 cP. For the additive compositions in the last two entries with only 15 or 0% PEG, and the remainder NMP, the OD was much lower for the precipitation studies at 5 mg/ml protein, indicating higher protein solubility. For these additive compositions and 150 mg/ml suspensions, viscosities were either very high, 287 cP, or not measurable, as a paste-like gel was formed. Thus, the additive compositions that cause significant protein precipitation at 5 mg/ml in FIG. 9, also are beneficial for producing lower viscosities. As the ratio of dissolved protein to micron-sized protein protein particles goes down, the viscosity is decreased. This decrease may be attributed to a reduction in solvation and electrosviscous forces, although further characterization would be needed to more fully describe the mechanism.

In Table 8, miscellaneous additive conditions beyond those in Tables 6 and 7. The aqueous solutions contained pure salt, pure PEG300, and mixtures of salts, PEG300 and water-soluble organic additives up to a total of 50% of the solution (Table 8). Syringeable aqueous-based IgG suspensions were obtained in all of these cases with a 25 G 1.5" needle. In each of these cases, micron-sized particles were formed given the IgG freezing concentrations of 40-55 mg/ml. For all the suspensions in this table, the presence of micron-sized particles was confirmed with the optical microscope (select samples shown in FIG. 11). The high molarity salt (1.5M) additive gave the lowest viscosity of 12.2 cP at an IgG concentration of 200 mg/ml (Table 8). At an IgG concentration of 200 mg/ml with trehalose, the next lowest viscosity was for the 50% PEG300 sample at 79 cP (Table 8). Adding 15% NMP and decreasing the PEG300 to 35% at a pH of 6.4, increases the suspension viscosity up to 104 cP (Table 8). A different organic additive with a similar dielectric constant, ethanol, at the same 15% level, gave a slightly lower viscosity at 92 cP (Table 4). As previously demonstrated for BSA, the various additive compositions that decrease the solubility of a protein below 5 mg/ml can often give highly precipitated suspensions and viscosities less than 100 cP at IgG concentrations greater than 100 mg/ml. Certain additive compositions allow such viscosities up to 200 mg/ml protein, and it may be expected that even higher protein concentrations may be achieved by further optimization.

As mentioned in Table 5, powders containing protein highly stable against monomer aggregation were achieved with or even without trehalose as a cryoprotectant. We also examined the protein stability after forming the suspensions. For the final suspensions, 10 μl of the suspension were diluted in pH 7.0 phosphate buffer necessary to give a final IgG concentration of ~1 mg/ml. The relative stability was measured as the difference between the % monomer after redilution when compared to the % monomer for the initial lyophilized particles upon reconstitution. For all of the examples in Tables 6-8, where trehalose was present at 0.5:1 or higher and without organic solvent (NMP or ethanol), the monomer was high, at least 97%. The % monomer was >100% in some cases, either because of experimental error or an actual increase in the monomer fraction relative to the as received starting bulk material. The high stabilities for systems with high PEG levels was not unexpected as PEG is known to help maintain the thermal stability of a protein. {Stevenson} High stabilities are shown in the last two rows of Table 4 for the two cases with a high salt concentration (1.5M ammonium sulfate). The high salt concentration produces very low protein solubilities and favors the presence of the micron-sized protein particles.

For the two studies without trehalose in Table 6 the protein aggregation was significant. After the powder with no trehalose was suspended, SEC shows approximately a 20% loss in % monomer to small aggregates (row 2 in Table 6). A smaller decrease in the % monomer of ~15% was seen for particles with an insufficient ratio of trehalose (0.25:1 trehalose to IgG ratio) (Table 6). Thus trehalose at a ratio of 0.5:1 of trehalose to IgG was required to maintain stability of the protein in the suspension, despite the fact that trehalose had a small effect on stability for the initial powers in Table 5.

The behavior is more complicated for the systems containing NMP and PEG. As shown in the first three rows in Table 7, the protein stability decreases with an increase in NMP concentration for a constant overall additive concentration of 50%. However, at a higher 1:1 IgG to trehalose ratio with the 35% PEG 300, and 15% NMP, the initial monomer was 98%. Thus, the higher ratio IgG to trehalose may compensate for the higher degree of organic additive (NMP) to maintain the stability.

The protein stability for the suspensions may be compared with those for protein in buffer without the addition of agents to lower the solubility. The power formed at 55 mg/ml initial protein (Table 5) was added to pH 6.4 buffer without any other additives. The resulting mixture was translucent and less turbid than in any of the entries in Tables 5-8. Upon centrifugation at 16,100 g, a precipitate was formed with a volume less than 10% of the total protein volume. Thus, most of the protein was dissolved. The % monomer was 70% for the same procedure as for the suspensions above. In contrast, the monomer was 97.1 for the same powder (55 mg/ml) at the 200 mg/ml level for an opaque white suspension of micron sized particles in Table 6. Thus, micron-sized particles of protein can be far more stable than proteins primarily in the dissolved state at high concentrations.

Stable as measured by SEC, highly concentrated aqueous based suspensions of a model IgG were created using particles that were frozen and lyophilized at high concentrations (40-55 mg/ml). This concentration range (40-55 mg/ml) made particles with a diameter of ~10-100 μm that were found to be greater than 98% stable by SEC. By stabilizing the particles with trehalose at a minimum ratio of 0.5:1 trehalose to IgG, the final suspensions were also found to preserve at least 92% of the original monomer percent. The solubility of the IgG was lowered to less than 5 mg/ml in the aqueous-based solvent by adding high salt (1.5 M ammonium sulfate), PEG300 (50% of solvent by volume), or a combination of PEG300 and ethanol or NMP (total 50% of solvent by volume). The apparent viscosity through a 25 g 1.5" syringe of the high salt suspension, where the solvent viscosity is still ~1 cP, was the lowest at approximately 12 cP for a 200 mg/ml stable (by SEC) IgG suspension. Overall, the stability of the model IgG and the low viscosities (less than 100 cP) through a 25 g 1.5" needle obtained for highly concentrated suspensions indicates a potential advancement in the subcutaneous delivery of protein therapeutics.

The delivery of concentrated proteins and peptides in the range of 100 to 400 mg/ml by subcutaneous injection through a 25 to 27-gauge needle becomes feasible for a stable solution or suspension with a viscosity below about 50 cP. Viscosities below this limit were achieved for suspensions of milled lysozyme microparticles in benzyl benzoate or benzyl benzoate mixtures with vegetable oils for up to 400 mg/ml protein. The protein molecules were stable against aggregation for at least 2 months and the solid particles in suspension were resuspendable after being stored at room temperature for a year. Correlations between the viscosity of the suspension and the volume fraction of particles indicate that the main source of interaction between the particles was simply due to the high concentration of particles with little effect from additional forces such as electrostatic repulsion, solvation of the particles or deviations of the particle shape from a spherical geometry. In contrast these additional forces can cause large increases in viscosities for colloidal protein molecules in aqueous solutions. Thus the lower solvent viscosities for highly concentrated protein suspensions relative to protein solutions may offer novel opportunities for subcutaneous injection.

As used herein, "stable proteins" refer to proteins that do not show instabilities such as denaturation or aggregation of the individual protein molecules in the dissolved state. These instabilities can be measured by techniques such as optical turbidity, dynamic light scattering, size-exclusion chromatography, analytical ultracentrifugation, and a protein dependant activity assays.

Solvents for use with the present invention include those in which the non-aqueous suspensions that produced stable particles not change in particle size over 2 months of storage with a protein solubility of less than 0.03 mg/ml. The solvent must also not cause an adverse affect on the stability of the protein particles. Stability of protein particles can be obtained for a non-aqueous solvent where the absorption of water into the particles in the suspensions is approximately equal to the absorption of water into particles exposed to ambient air conditions at the same relative humidity. In addition, a non-aqueous solvent should have a low dielectric constant (less than 37.5) to prevent attractive forces between the particles to cause caking of the particles at the bottom of the container causing the suspension to be unable to be resuspended.

The objective of this study was to produce a highly concentrated protein suspension for delivery of high dosages of monoclonal antibody by subcutaneous injection via a 25- to 27-gauge syringe. Suspensions of lysozyme particles smaller than 37 μm with concentrations from 50 to 300 mg/ml were formulated with a 50/50 volume mixture of the pharmaceutically acceptable solvents safflower oil and benzyl benzoate. This solvent mixture was within the approved range published on the FDA's Inactive Ingredients List.[18] While benzyl benzoate is less viscous than safflower oil, which facilitates formation and injection of the dispersions, it is not currently accepted for injection by the FDA as a pure solvent; however, indications of lack of toxicity suggest it may be approved in the future. The apparent viscosities for formulations in the approved solvent mixture as well as pure benzyl benzoate will be shown to be in an acceptable range up to a concentration of at least 300 mg/ml and to correlate with theoretical viscosities of suspensions according to the Krieger-Dougherty equation. The necessity to obtain a uniform dose is addressed through measurements of the settling rate and confirmed by concentration measurements of aliquots of the suspension. Colloidal stability of the particles and the stability of the protein molecules are addressed by measurements of particle and protein aggregation over time and are further confirmed by analyzing the moisture content in the various suspensions.

Lysozyme in lyophilized powder form was purchased from Sigma Chemical Company (St. Louis, Mo.). ACS grade acetonitrile and USP grade ethanol were used as received from Fisher Chemicals (Fairlawn, N.J.). Food grade olive oil and safflower oil were purchased for initial tests from the grocery store. Benzyl benzoate was obtained from Acros Organics (New Jersey) and N.F. grade ethyl oleate from Spectrum Chemical Corp. (Gardena, Calif.).

Lysozyme powder as received was dry milled with a porcelain mortar and pestle for several minutes. The milled powder was then sieved through a number 400 mesh and particles smaller than 37 μm were collected. Samples were then weighed and added to a measured amount of benzyl benzoate or a premixed 50/50 volume mixture of benzyl benzoate and safflower oil. Each vial was then shaken by hand to disperse the powder evenly through the suspension.

Particle size was measured by multiangle laser light scattering with a Malvern Mastersizer-S (Malvern Instruments, Ltd., Worcestershire, UK). The milled and sieved powder sample size was measured as a suspension in acetonitrile in a large recirculation cell (~500 ml) and immediately after being added to ethanol in a small batch cell (Malvern, Worcestershire, UK, ~15 ml). In each case the obscuration during the measurement was between 10-15%. After storing the suspensions for 2 months at room temperature, the particle size was measured again immediately after shaking and diluting the sample in ethanol in the small batch cell.

The viscosity was measured as the time to draw 1 ml of the sample into a syringe with a 25 g ⅝" or 27 g ½" needle. Each measurement was made at least 3 times and averaged. Liu et al. found this measurement time to be correlated linearly to viscosity. From known viscosities of each pure liquid, benzyl benzoate, ethanol, ethyl oleate and olive oil, the correlation between the time to draw 1 ml of solution and the viscosity was found for each needle size to give an $r^2$ value greater than 0.999. The apparent viscosity of the suspensions in each pure solvent was calculated from these correlations and the values for the two separate needle sizes were averaged to give a final average apparent viscosity of each sample. Additional samples of the solvent mixture of benzyl benzoate and safflower oil were made at 10, 20, 30, 40, 50, 60, 70, 80, and 90 percent benzyl benzoate by volume. The viscosity of each sample was calculated as described above.

The settling rate of the particles in the solvents was measured by shaking up the suspension in a test tube 13 mm in diameter. Pictures were taken with a standard digital camera after 10, 30, 60, 90, 120, 150, 180, 210, 240, 1200, and 1440 minutes. To measure the final settling volume of the samples, the vials containing the suspensions were left undisturbed for 4 months and images of the settled suspension were taken. All images were analyzed using ImageJ software for the distance from the meniscus to the settling front. The maximum volume fraction for the settled suspension was defined by dividing the volume fraction of particles in the overall suspension by the ratio of the volume containing particles after settling for 4 months to the overall volume.

The concentration of lysozyme in an aqueous solution was measured following the protocols for the Micro BCA Protein Assay. Each sample was measured in triplicate with relative standard deviations (% RSD) less than 2% in a General Assay 96 well plate (see statistical analysis below). The absorbance was measured at 562 nm in a spectrophotometer. A standard curve of untreated lysosyme was prepared at concentrations between 2 and 30 μg/ml.

Partitioning and dissolution of lysozyme from the concentrated suspension was measured in a pH 7.4 potassium phosphate buffer. The USP paddle method was used with a VanKel VK6010 Dissolution Tester with a Vanderkamp VK650A heater/circulator. 900 ml of dissolution media was preheated in large 1 L capacity dissolution vessels (Varian Inc., Cary, N.C.) to 37° C. A sample of the concentrated suspension giving a total of 18 mg of lysozyme was added. At time increments of 2, 5, 10, 20, 40, 60, 120 and 240 minutes, 1 ml samples were taken and analyzed using the Micro BCA protein analysis mentioned earlier.

0.1 ml of the concentrated lysozyme suspension was added to a test tube with 4 ml of DI water. This mixture was then gently mixed and left for 3 days for the protein to partition to the water phase. The water phase was then separated and a sample was diluted and tested for concentration using the Micro BCA Protein Assay as mentioned above. The remaining aqueous solution was diluted to a concentration of 1 mg/ml. This solution was tested for optical density using at least 3 300 μl aliquots in a 96-well plate and analyzed using the μQuant spectrophotometer at 350 nm. A standard lysozyme aqueous solution was made at 1 mg/ml concentration and exposed to the pure benzyl benzoate solvent and the benzyl benzoate and safflower oil solvent mixture for 3 days and measured as the standard for oil-water interface induced aggregation of the protein. The aqueous solution without being exposed to any organic solvent was also measured immediately after it was made and used as the standard absorbance for all measurements.

Three separate 0.1 ml aliquots of the resuspended concentrated lysozyme suspensions were added to test tubes with 8 ml of DI water. These mixtures were then gently mixed and left for 1 day for the protein to partition to the water phase. The aqueous phase was then separated and diluted to a theoretical concentration of 20 μg/ml if 100% of the protein partitioned. The actual concentration was then analyzed using the Micro BCA protein assay mentioned above.

Karl Fischer Moisture Analysis. After being stored for four months, a sample of 0.1 ml of the redispersed concentrated suspension was inserted using a 19-gauge needle through the septum of the titration cell of an Aquatest 8 Karl-Fischer Titrator (Photovolt Instruments, Indianapolis, Ind.). Each suspension, pure benzyl benzoate and the benzyl benzoate and safflower oil solvent mixture was measured in triplicate and averaged.

Polarity Determination. An aliquot of the suspension was diluted with the solvent until individual particles were visible on a slide through an optical microscope (Bausch & Lomb, 10× magnification). Microelectrophoresis was used to determine if a charge was present on the particles. The diluted particle dispersion was placed between two parallel wire electrodes (0.01-in. diameter stainless steel 304 wire, California Fine Wire) spaced 1 mm apart. The electrodes were secured to a glass microscope slide and observed by optical microscopy. A potential of 10-100 V was applied with the polarity of the electrodes switched every 15-60 sec.

Samples for protein concentration, Karl Fisher moisture analysis, suspension uniformity, optical density, and rate of lysozyme partitioning to water were measured in triplicate to determine the mean, standard deviation and the relative standard deviation (std. dev./mean).

Figure 12:
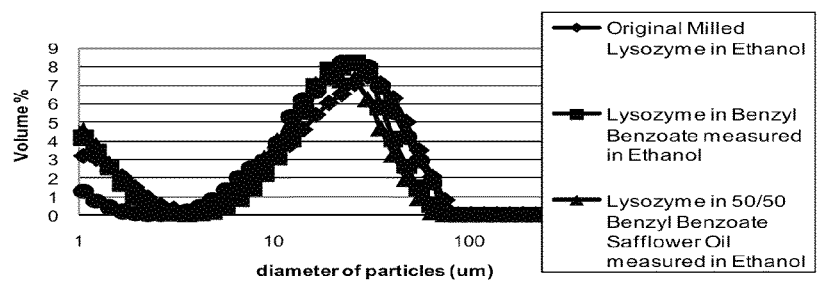
FIG. 12. Volume % of particles versus size measured for the original milled particles in acetonitrile and ethanol and after 2 months of storage for the suspensions in pure benzyl benzoate and a mixture of benzyl benzoate and oil both measured immediately after being diluted in ethanol to 10-15% obscuration by light scattering.

For lysozyme particles that were milled by mortar and pestle and sieved through a number 400 sieve, the average particle size was approximately 20 μm, according to light scattering measurements (FIG. 12). A minor secondary submicron peak was also visible in all measurements. However, since the 15 ml small batch cell is only calibrated for particle sizes down to 500 nm, this peak was not included in the analysis. The vial containing the particles and solvent is then shaken by hand and the particles disperse to form a uniform suspension (FIG. 13B). When the particle suspensions are allowed to sit undisturbed, they settle slowly enough to remain partially suspended even after 24 hours (FIG. 13C) and the highly concentrated suspension takes up a significant portion of the volume even after 2 months (FIG. 13A).

Viscosity of Solvent Mixture and Suspensions. Using the known viscosities of pure solvents, a correlation between the time to draw 1 ml of the sample and viscosity was generated. This type of correlation has been described by Shire and coworkers on the basis of the Hagen-Poiseuille equation[5-7]

$$<v> = \frac{R^2}{8\eta}\left(\frac{|\Delta P|}{L}\right) \qquad \text{Eq. 2}$$

where $v$ is the velocity, R is the inner radius of the needle, $\eta$ is the viscosity, and $\Delta P/L$ is the average pressure drop over the length of the needle. Ensuring that the average pressure drop over the length of the needle remains constant for each sample by maintaining the same suction pressure inside the syringe, the inverse of the velocity of the fluid multiplied by the cross-sectional area gives the time to draw up a specified volume of liquid, in this case 1 ml. This time is proportional to the viscosity as shown by the Hagen-Poiseuille equation.

Figure 14:
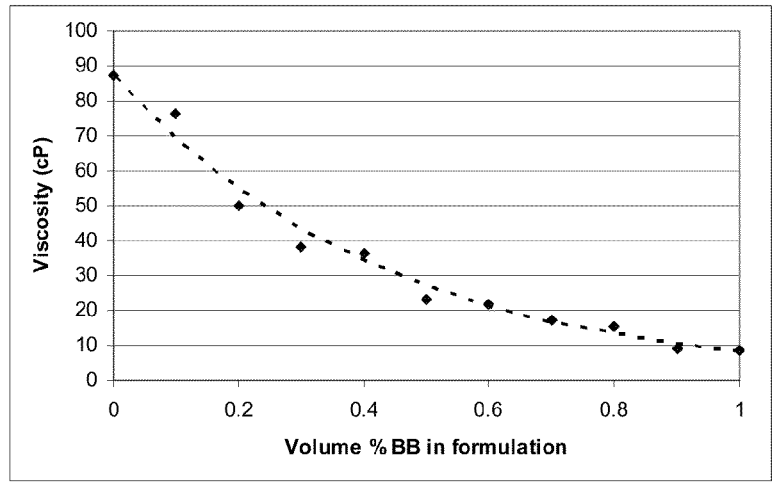
FIG. 14 Viscosity of a solution of benzyl benzoate and safflower oil at room temperature at varying concentrations.

The measured viscosities of the solvent mixtures of benzyl benzoate and safflower oil are shown in FIG. 14. In this case, since the minimum and maximum values are the for the pure solvents, the generalized mixing rule should follow the form $$f(\eta_m)_L = \sum_i x_i f(\eta_i)_L \qquad \text{Eq. 3}$$

where $\eta_m$ is the viscosity of the mixture, i is the number of components, $x_i$ is the liquid volume, weight, or mole fraction, and $\eta_i$ is the viscosity of the $i^{th}$ component. $f(\eta)_L$ can be $\ln(\eta_L)$, $1/\eta_L$, or another typical equation.[20] In this case, the correlation most closely associated with the experimental results was when $f(\eta)_L$ was $\ln(\eta_L)$. This theoretical result is shown by the dotted line in FIG. 14.

Figure 15:
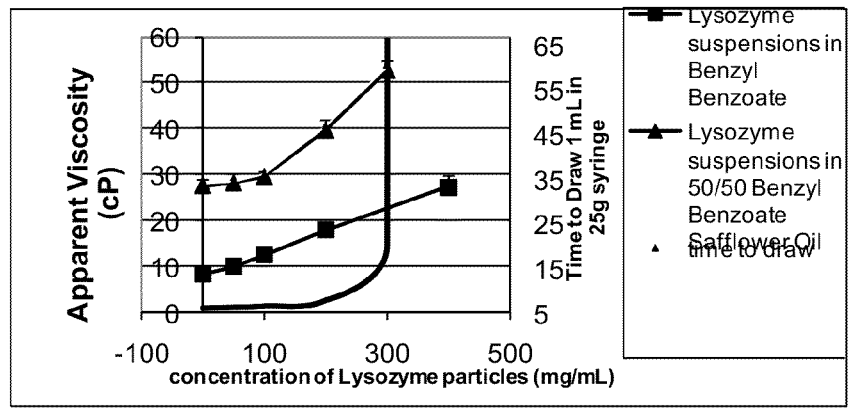
FIG. 15 The apparent viscosity as a function of concentration of particle as suspensions in the non-aqueous solvents and the theoretical viscosity of an aqueous lysozyme solution.
Figure 16:
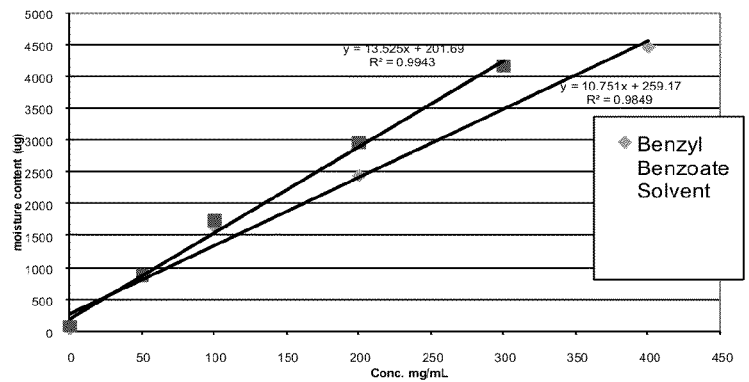
FIG. 16 Karl Fisher moisture content analysis of the suspensions.

The apparent viscosities of the suspensions with increasing concentration were measured for both the pure benzyl benzoate system and the solvent mixture of 50/50 benzyl benzoate and safflower oil. The resulting viscosities, averaged from the measurements using two syringe sizes (left y-axis), and the time to draw 1 ml from the 25-gauge syringe (right y-axis) were plotted against the concentration of lysozyme particles (FIG. 15). The correlation of the apparent viscosity with the free solvent volume fraction was modeled using the Kreiger-Dougherty equation $$\frac{\eta}{\eta_o} = \left[1 - \left(\frac{\phi}{\phi_{max}}\right)\right]^{-[\eta]\phi_{max}} \qquad \text{Eq. 4}$$

where $\eta$ is the apparent viscosity of the dispersion, $\eta_o$ the solution viscosity, $\phi$ the volume fraction of particles, $\phi_{max}$ the maximum packing fraction, and $[\eta]$ the intrinsic viscosity. $\phi_{max}$ was approximated after gravitational settling of the particles over 4 months. It was approximately 0.50 for the pure benzyl benzoate solvent solution and 0.52 for the benzyl benzoate and safflower oil solvent for low shear rates Using these values, the intrinsic viscosity of the suspension, $[\eta]$, was determined to be 2.7 for the pure benzyl benzoate suspensions and 2.3 for the benzyl benzoate and safflower oil suspensions.

The stability of the particles in suspension was measured by numerous different techniques. First the settling rate was calculated and compared to the theoretical Stokes settling rate $$U_s = \frac{2r^2\Delta\rho g}{9\eta_o} \qquad \text{Eq. 5}$$

where r is the radius of the particles, $\Delta\rho$ is the difference in densities between the solvent and the particles, and g is acceleration due to gravity. For a high concentration of particles, the particle crowding will reduce the settling rate to yield $$U = U_s(1-\phi)^{6.55} \qquad \text{Eq. 5}$$

This modified Stokes settling rate and the experimentally measured values were found to be within a factor of two for most concentrations lower than 300 mg/ml as shown in Table 1. However, for a concentration of 400 mg/ml the values are an order of magnitude lower than the predicted rate (Table 9).

TABLE 9

Comparison of experimental settling rates and settling rates quantified by the modified Stokes settling equation accounting for particle interactions (eq. 4, 5).

| Formulation | volume fraction of particles (Φv) | Experimental settling rate (cm/min) | Modified Stokes settling rate (cm/min) |
|---|---|---|---|
| 50 mg/mL Lys in 50/50 Safflower Oil and Benzyl Benzoate | 0.03515 | 0.0308 | 0.0141 |
| 100 mg/mL Lys in 50/50 Safflower Oil and Benzyl Benzoate | 0.0703 | 0.0220 | 0.0111 |
| 200 mg/mL Lys in 50/50 Safflower Oil and Benzyl Benzoate | 0.1406 | 0.0053 | 0.0066 |
| 300 mg/mL Lys in 50/50 Safflower Oil and Benzyl Benzoate | 0.2109 | 0.00071 | 0.0038 |
| 50 mg/mL Lys in Benzyl Benzoate | 0.03515 | 0.0651 | 0.0373 |
| 100 mg/mL Lys in Benzyl Benzoate | 0.0703 | 0.0274 | 0.0293 |
| 200 mg/mL Lys in Benzyl Benzoate | 0.1406 | 0.0087 | 0.0175 |
| 400 mg/mL Lys in Benzyl Benzoate | 0.2812 | 0.00052 | 0.0054 |

The suspension uniformity was further quantified by the percent extracted into an aqueous phase. Initially the rate of partitioning of the lysozyme into the aqueous phase was determined to require approximately 60 minutes. Three aliquots from the resuspended samples were placed in separate test tubes and allowed to partition to the aqueous phase for 1 day to ensure complete partitioning. The aqueous phase was then diluted approximately 1000 times, and the concentration of protein was measured. The results show that even with a small volume (8 ml) of aqueous phase exposed to 0.1 ml of the concentrated non-aqueous suspension at least ¾ of the protein partitions into the aqueous phase in 24 hours (Table 10). The % RSD values were typically below 5% indicating reasonable uniformity of the protein particles within the redispersed suspension. The % RSD was slightly larger for the highly concentrated 300 mg/ml sample in the mixed solvent.

TABLE 10

Percent of sample recovered in aqueous phase and % relative standard deviation (% RSD) of 3 samples.

| Solvent | Concentration (mg/ml) | % recovered in aqueous | % RSD |
|---|---|---|---|
| Safflower Oil and Benzyl Benzoate | 50 | 77.2% | 2.21% |
| Safflower Oil and Benzyl Benzoate | 100 | 78.5% | 6.61% |
| Safflower Oil and Benzyl Benzoate | 200 | 85.8% | 3.20% |
| Safflower Oil and Benzyl Benzoate | 300 | 76.2% | 9.45% |
| Benzyl Benzoate | 50 | 85.2% | 1.52% |
| Benzyl Benzoate | 100 | 96.9% | 3.46% |
| Benzyl Benzoate | 200 | 92.2% | 3.65% |
| Benzyl Benzoate | 400 | 81.2% | 4.29% |

The aggregation of the particles exposed to the non-aqueous solvent was also tested to ensure that growth of the particles is not occurring at a sufficient rate to jeopardize the storage of the samples. The original particle size was measured via light scattering immediately after the particles were sieved and resuspended in both acetonitrile, where lysozyme is very insoluble, and ethanol, where lysozyme is slightly soluble. The uniformity of the two measurements ensures that the time scale of the measurement is much quicker than the time scale of growth of the particles in ethanol (FIG. 12). Following 2 months of storage, the samples were diluted in ethanol and immediately tested. The particle size was found to be essentially constant during storage (FIG. 12). The visual inspection of one formulated suspension after storage for a year and redispersion by shaking confirms that the particles could be redispersed.

The potential effect of electrostatic repulsion on the particle stability was tested. However the lysozyme particles did not display organized movement when the voltage was changed from 10 to 100 for two electrodes spaced 1 mm apart in the benzyl benzoate solvent.

Protein aggregation was investigated by measuring the optical density on sample aliquots that partitioned from the organic to the water phase. The protein was diluted to a concentration of 1 mg/ml. Additional lysozyme samples in an aqueous solution at the same concentration were exposed to the solvent to measure the effect of the oil-water interface on aggregation. All these solutions were checked for large protein aggregates by comparison with a fresh lysozyme solution at the same concentration. No aggregates were found since the absorbance at 350 nm was within 1% for the standard and all samples and therefore within the error of the study.

Quantification of the moisture content may be used to determine the free and bound water in the suspension. The moisture content was measured for each suspension after being exposed to atmospheric conditions for 2 months. The linear correlations found between the moisture content and suspension concentration indicates that the moisture is directly associated with the protein (FIG. 16). The benzyl benzoate solvent contains an average of 20 μg of water per 0.1 ml of solution or approximately 0.02% by weight. The safflower oil and benzyl benzoate mixture contains approximately 74 μg of water in the same volume sample or approximately 0.074%. The sample with the highest concentration of protein in benzyl benzoate, 400 mg/mL, contained the most moisture, an average of 4450 μg of water per 0.1 ml of solution giving an absolute maximum concentration of 4.5% by weight of the suspension after being stored for 2 months.

In addition to protein and particle stability, the other key criterion is that the suspension's apparent viscosity must be low enough for injection through a syringe. For subcutaneous delivery, 50 cP is an appropriate maximum viscosity where it will take approximately 20 seconds for 1 ml of the suspension to be expelled via a 26-gauge syringe. From FIG. 15, the highest apparent viscosity measured was approximately 50 cP, where it took approximately 55 seconds to draw 1 ml into a 25-gauge syringe. The disparity in the times measured reflects the smaller suction force to draw the volume into the syringe relative to the force needed to expel the solution from the syringe. In addition, these concentrated suspensions are considered to be shear thinning since the flow of the suspension will produce a more favorable rearrangement of the particles. For example, as the shear rate increases, spherical particles that were initially randomly packed ($\phi max=0.64$) become more ordered and pack tighter, giving a higher maximum packing fraction around 0.71. As a result, at the higher shear rate associated with expelling the volume, the measured apparent viscosity of the suspensions will decrease and will remain below the maximum for potential subcutaneous delivery.

Further analysis of the viscosity of the suspensions using the Kreiger-Dougherty equation can give an indication of the effect of interparticle forces in the suspension. The initial equation for the viscosity of a dilute suspension derived by Einstein takes into account the particles and assumes that the particles are solid spheres and their concentration is low enough for the particles to be treated individually ($\phi$<0.1). This gives a first order equation where the volume fraction of the particles is related to the viscosity ratio of the suspension over the solvent with a slope of 2.5. In more general terms, this slope signifies the increment of viscosity due to the addition of dispersed particles and is also called the intrinsic viscosity, [$\eta$]. For more concentrated suspensions, accounting for particle crowding and the maximum packing fraction of the suspension ($\phi$max) results in the Krieger-Dougherty Equation (Equation 5).31,32 In this case, the intrinsic viscosity term can vary from the Einstein coefficient value of 2.5 depending on the effects of solvation, varying shapes, and electrostatic forces as well as the shear rate. Since the values for the intrinsic viscosity of the benzyl benzoate and the benzyl benzoate and safflower oil mixture suspensions are close to the original Einstein derived 2.5, the effects of solvation, varying shapes, and electrostatic forces may be considered to be negligible assuming the shear rate is low and can be approximated as zero. The lack of electrostatic effects was not surprising given the tendency for ion pairing in the solvent with a dielectric constant of only 4.8. This is further confirmed with the lack of electrophoretic mobility measured above. If the particles are solvated by the solvent the volume fraction would increase by $$\frac{\phi_{solvated}}{\phi_{dry}} = \left[1 + \left(\frac{m_{1,b}}{m_2}\right)\left(\frac{\rho_2}{\rho_1}\right)\right] \quad \text{Eq. 7}$$

where $m_{1,b}$ is the mass of the bound solvent, $m_2$ is the mass of the particle, $\rho_2$ is the density of the particle and $\rho_1$ is the density of the solvent. In the case of the Krieger-Dougherty equation, this increase is absorbed into the [$\eta$] term, increasing the measured intrinsic viscosity. The deviations of the particles from spherical shape has a strong effect on the maximum packing fraction and on the intrinsic viscosity. For example, glass fibers of varying axial ratios, 7, 14 and 21 increase in intrinsic viscosity from 3.8 to 5.03 to 6.0, respectively, and decrease in maximum packing fraction from 0.374 to 0.26 to 0.233. Since a large macromolecule, such as a monoclonal antibody in solution, can be approximated as a small colloid, similar viscosity analysis can be conducted. In this case, previously published values for the increase in viscosity of a solution containing a monoclonal antibody at varying concentrations was used giving a final value of [$\eta$] of 45 from analysis using the Krieger-Dougherty equation (Table 11). However, the analysis of protein solutions is typically done using mass concentrations (g/ml) rather than volume fractions, leading to values of the intrinsic viscosity in units of cm3/g and slightly different derived higher order relationships between the viscosity of a protein solution and the aqueous solvent. A hard quasispherical model $$\frac{\eta}{\eta_o} = \exp\left(\frac{[\eta]c}{\left(1 - \frac{k}{\upsilon}[\eta]c\right)}\right) \quad \text{Eq. 8}$$

where c is the mass protein concentration, k is a crowding factor accounting for high concentrations of the protein and $\upsilon$ is the Simha parameter accounting for the change in shape from a sphere, is derived from the same power series as the Krieger-Dougherty equation; however, using concentration rather than volume fraction as the x component. As a result, it leads to a value of 6.9 cm$^3$/g for the intrinsic viscosity of a monoclonal antibody and a $\kappa/\nu$ value of 0.533. For various proteins, the value of the intrinsic viscosity varies from approximately 2.7 for lysozyme to over 200 cm$^3$/g. This model has been shown to accurately predict the viscosities of hemoglobin, bovine serum albumin, and two various monoclonal antibodies where long range electrostatic forces were found to play a negligible role in the viscosity versus concentration. Even for lysozyme, a protein with a very small axial ratio, 1.5, this model shows a dramatic increase in viscosity around a concentration of 300 mg/ml (FIG. 15). Therefore, for various monoclonal antibodies, BSA, and hemoglobin that can described by the hard quasispherical model and have higher axial ratio than lysozyme (eq. 8), the rapid increase in viscosity will be more dramatic and occur at a lower concentration. For these solutions, the viscosity increase is due not only to particle crowding but also to the excluded volume effects of solvation and deviation of the shape from a sphere. This strong deviation is not seen for particles in suspension at the same concentrations because they are fairly spherical, are not hydrated by the solvents, and the density of a protein is typically around 1.35 g/cm$^3$ leading to a lower volume fraction for the respective concentration.

TABLE 11

Comparison of the two solvent systems of suspensions and the high concentrated solution monoclonal antibody for the exponents for the Krieger-Dougherty equation, the experimental maximum packing fraction, and intrinsic viscosity.

| Solvent system | Exponent for Krieger-Dougherty equation −[$\eta$]$\Phi_{max}$ | Maximum volume packing fraction $\Phi_{max}$ | Intrinsic viscosity [$\eta$] |
|---|---|---|---|
| Benzyl benzoate suspension | −1.362 ± 0.09 | 0.50 | 2.7 |
| 50/50 Safflower Oil and Benzyl Benzoate suspension | −1.149 ± 0.06 | 0.52 | 2.3 |
| Mab1 solution in aqueous solution | −45.27 ± 0.61 | 1 | 45.3 |

Figure 17:
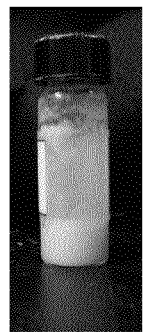
FIG. 17 Image of a suspension taken immediately after formulation.

The viscosities of concentrated suspensions up to 300-400 mg/ml of milled particles of the model protein, lysozyme, were small enough for subcutaneous injection through a 27-gauge needle. The protein molecules were stable against aggregation and the particle size did not vary for at least 2 months when stored at atmospheric conditions. The apparent viscosity was correlated with volume fraction at all conditions according to the Krieger-Dougherty equation. Full settling of the particles was found to take well over 24 hours, which gave sufficient time for a uniform aliquot to be taken and analyzed. The results indicated sufficient suspension stability to allow for accurate dosing, either for, single injection or multiple injection applications. Overall, the colloidal stability and dose uniformity of the lysozyme microparticle suspensions, along with the acceptably low viscosities, indicates a potential advance for subcutaneous delivery of therapeutic proteins. For highly concentrated proteins in solution, various forces including electrostatic repulsion, solvation forces, and deviations of the particle shape from a spherical geometry can cause large increases in viscosity, whereas these forces have almost negligible effects for the current protein suspensions, resulting in much lower viscosities.

The objectives of this example are to: (1) use various particle engineering techniques to produce protein particles to form suspensions in nonaqueous and aqueous solvents, (2) to find efficient ways to form the particles in vials or transfer the particles to vials, (3) to determine the particle size, colloidal stability and viscosity of the suspensions, and (4) determine the stability of the protein molecules with regard to denaturation and aggregation. The relevant particle engineering techniques include milling, spray drying, precipitation, and thin film freezing. The feasibility of delivering proteins and peptides by subcutaneous injection depends on formulating a sufficiently low viscosity product that is syringeable through a 25 to 27-gauge needle but contains the necessary high concentration of the active protein or polypeptide to give a full dose in less than 1.5 ml of volume. Desired viscosities have been made with protein suspensions with up to 400 mg/mL.

Of primary importance in the formulation of a stable suspension system that contains a high concentration of the monoclonal antibody and a sufficiently low viscosity is the formation of stable appropriately sized monoclonal antibody particles. Previously, a suspension was formulated with ~10-20 μm milled lysozyme.1

In addition to milling, protein particles may be formed with thin film freezing (TFF), previously disclosed to produce stable nanoparticles of proteins2, to produce similar micron-sized particles, depending upon the feed concentration. Since the monoclonal antibody will come in solution form, TFF will be a significantly less destructive process, causing only potential freezing stress whereas lyophilization followed by milling and sieving the particles will expose them to freezing, heating and mechanical stresses which can lead to denaturation. Proposed work will include tuning the TFF process to produce the specified particle size by altering the feed concentration within the solubility limits of the Mab and adding cryoprotecting sugars such as trehalose, varying the solvent (currently pure DI water with a buffer) to include a percentage of ethanol and various buffers and other excipients necessary for a subcutaneous injection, and examine freezing directly into appropriate vials for subcutaneous injection formulation.

Various techniques will be utilized to transfer the protein particles into the vials. The goal will be to simplify processing steps and to maintain sterile conditions. The first method is to transfer lyophilized powder to the vials as a solid. A second method is to transfer the protein to the vials while still in the frozen state. Particle size data was obtained to demonstrate each of these methods using the TFF process (Table 12).

TABLE 12

Comparison of particle size distributions, measured by multi-angle light scattering of protein particles suspended in acetonitrile, from different concentration distributions of TFF. The particles were transferred to vials either after lyophilization or after only freezing.

| Sample | Freezing Method | Particle Size (dV10, dV50, dV90) |
|---|---|---|
| High concentration BSA | Frozen in vial | (18.93, 32.88, 53.07) |
| High concentration BSA | Separated after lyophilization | (0.32, 17.95, 45.07) |
| High concentration LYS | Separated after primary drying lyophilization | (0.23, 13.60, 31.30) |
| High concentration LYS | Separated after freezing | (0.31, 13.17, 28.57) |
| Low concentration LYS | Frozen in vial | (0.12, 0.39, 2.27) |

Once appropriate stable particles are made, an appropriate solvent system must be found. In this case, both aqueous and non-aqueous based systems will be analyzed. A stable, low viscosity formulation of milled lysozyme in the pure non-aqueous solvent benzyl benzoate and the solvent system benzyl benzoate and safflower oil have been previously analyzed1 and will be analyzed further in a suspension containing the Mab particles described above. To overcome the instabilities of the protein or polypeptide in a highly concentrated aqueous solution and the increase in viscosity caused by soluble aggregates and hydration, the main objective of this study was to formulate a protein suspension in a non-aqueous solvent or solvent mixture using the model protein lysozyme that is syringeable through a 27-gauge needle and at a concentration greater than 100 mg/ml. The suspensions formulated were found to remain syringeable up to at least a concentration of 300 mg/ml. Protein and particle stability remained for at least 2 months indicating a potentially stable protein product. Protein particles in suspension were also found to be resuspendable after being stored at room temperature for a year. Correlations between the viscosity of the formulation and the increasing volume fraction of particles indicates that the main source of interaction between the particles is due to particle crowding and no additional forces such as electrostatic repulsion, solvation of the particles from the solvent, or deviations of the particle shape from spheres are used to maintain the stability of the suspension.

However, the main focus will be on aqueous solvents, whereas the nonaqueous solvents will be of secondary interest. An aqueous solvent system is slightly more complicated to formulate and must include: (1) an agent to decrease the solubility of the Mab in water (if solubility is greater than 20 mg/mL); (2) an antifoaming agent to prevent the concentrated suspension from producing a foam when the solvent is added; and (3) additional excipients to maintain the stability of the Mab and the final suspension product for a sufficient period of time.

Agents that can be added to decrease the solubility of a protein in water include high concentrations of salts such as sodium sulfate and ammonium sulfate, complexing agents including zinc, water soluble polymers such as PEG, various organic solvents such as ethanol and other surfactants such as Tween 20. Addition of salts increases the ionic strength of the solution which decreases the solubility of the hydrophibic groups of a protein. However for subcutaneous injectable delivery, a solution that is not isotonic will increase the pain upon injection, potentially leading to noncompliance. Therefore, alternatives to decrease the solubility with other additives can be advantageous. A polyethylene glycol (PEG) and water mixture has also been demonstrated to that similar "salting out" effects of salt and are more readily allowed in injectable formulations. Different molecular weight PEGs will be tried since lower molecular weight PEGs can be formulated to much higher concentrations for additional solubility decrease however higher molecular weight PEG have been found to increase the thermal stability of a protein. Tween 20 at a 1% (w/v) concentration has been demonstrated to cause precipitation of the hydrophobic protein Humicola-lanuginosa lipase5 which may prevent solubilization of the added Mab particles in suspension and create another alternative way to formulate the suspension. Additional excipients, such as water soluble non-aqueous solvents, where the Mab is only slightly soluble will also be tried including ethanol, propylene glycol, and dimethylacetamide.

Successful higher concentration formulations of low viscosities with salt and PEG formulations have been made in aqueous media (Table 13). Initial particle size measurements as well components are also disclosed. These formulations have been found to contain particle stability for at least 1 hr (FIG. 17); long time stability has not been investigated. Preliminary data indicate that the viscosities of some of the aqueous suspensions were sufficiently low for 25 gauge needles.

TABLE 13

Protein used, concentration, substance added to decrease solubility, preliminary viscosity measurement, preliminary particle size for successful aqueous based formulations.

| Protein and concentration | Agent to decrease protein solubility | Viscosity measurements | Particle size |
|---|---|---|---|
| 150 mg/ml BSA | PEG 300 aqueous solution | 57.5 cP | (0.40, 13.98, 26.82) |
| 250 mg/ml LYS | Salt aqueous solution | 5.7 cP | (0.27, 10.90, 26.91) |

Foaming of aqueous dispersions of proteins has been observed in a 1.0M sodium sulfate aqueous solvent suspension when the liquid was added to the dried TFF particles. Foam stability of an aqueous suspension of proteins and fat particles was reduced significantly with the addition of the different Span excipients where it was hypothesized to increase bubble coalesance. A trial using SPAN® 80 successfully broke the foam when added to a concentrated dispersion of BSA in a 1.0M Sodium Sulfate solution, leaving a low viscosity, highly concentrated suspension. Other surfactants will be used both in the particle formation and in the final formulation stage to resolve the foaming issue. In addition, other excipients must be added to complete the formulation of a pharmaceutically acceptable suspension to be administered subcutaneously. To stabilize the protein, surfactants such as Tween 20 and Tween 80 can be added if necessary. To create a final aqueous dispersion, buffering agents, antioxidants, and antimicrobial agents may be added.

Final formulated suspensions will then be tested for viscosity using the time to draw 1 mL of solution up a syringe with a 25- then 27-gauge needle. As demonstrated previously, the viscosity approximated with this measurement is reasonable with by both theoretical and previous results (above). In addition, settling rate measurements, images taken by optical microscopy, particle size measurements by multi-angle laser light scattering and electrophoretic mobility measurements will be used to characterize the stability of the suspension. The settling rate can be useful to determine the uniformity of the suspension over a period of time, in addition to aliquots of the suspension removed randomly and analyzed for protein concentration. In addition, the images taken by optical microscopy can show the dominant forces on the particles at lower concentrations and whether the particles are aggregating, flocculating or repulsing. Particle size measurements over time will show the effects of Oswald ripening and coagulation of particles. To complete the study, the electrophoretic mobility of the particles will be measured and quantify the zeta potential, which will determine the electrostatic stabilization of the particles in the suspension.

The final step is to determine the stability of Mab in the formulated suspension. For aqueous based suspensions, appropriate dilutions must be run to produce a solution of the Mab at the necessary concentration for analysis. The Mab in solution will also be separated from the suspended particles and both will be analyzed separately for stability. For non-aqueous based suspensions an aliquot with sufficient Mab concentration must be exposed to pure water or a suitable buffer to allow the suspended particles to partition to the aqueous phase in solution without denaturing on the oil-water interface. As has been done previously, suspensions will be exposed to the appropriate aqueous buffer for 1-3 days to allow slow partitioning and minimal exposure to the potentially denaturing oil-water interface.1 In addition, standards will be run to ensure that the measurements are an accurate representation of the suspended particles.1 The stability of the Mab can then be characterized by a variety of techniques including size-exclusion chromatography (SEC), dynamic light scattering (DLS), analytical ultracentrifugation (AUC), and optical turbidity for soluble and insoluble aggregates.

Moisture content of both the dried powder and the reconstituted non-aqueous suspension will be analyzed over time to determine the effect of excess water on the stability of the formulation. As has been noted in previous experiments, at low levels of protein hydration, the water sorption over time in a non-polar or moderately polar organic solvent is similar to that from the vapor phase itself.12 In addition, a Mab specific ELISA assay can be run to demonstrate the % activity of the Mab after formulation to analyze misfolding and denaturation of the Mab. This technique has been used previously to observe the resulting binding affinity of an IgG after reconstitution. FTIR can also be run to determine any Mab-excipient interactions with any part of the final formulation.

Production of particles by film freezing in vials. In many particle formation processes, the transfer of solids from various surfaces to vials for delivery of the final dosage form presents problems. It is necessary to maintain sterile conditions and it can be difficult to determine and control the exact amount of particles transferred. In addition, the particle size may change during handling. It would be desirable to produce the particles directly within the vial the final dosage form will be stored in. This process of direct freezing and particle production within a vial is practiced in conventional tray lyophilization. However, the slow freezing rates by heat transfer through the shelf to the vial leads to particles typically on the order of hundreds of microns. The current technique provides a means to produce and control sub-micron and micron sized particle distributions.

A method is provided for forming particles of substances inside vials, the method comprising: (a) introducing a liquid solution of the substances inside a cylindrical vial; (b) immersing the cylindrical vial into a liquid coolant while rotating it horizontally until the liquid has frozen as a film in the vial's internal walls; (c) removal of the solvent by lyophilization or by extraction of the frozen solvent into a second solvent.

Thus, the current invention provides an alternative to freeze much more quickly with a submersion of the vials in a cryogenic liquid than in the case of tray lyophilization. The more rapid freezing on the order of 20 s can result in sub-micron particles. The thickness of the freezing liquid, in the range of 0.2 to 4 mm, facilitates the rapid freezing. The vials may be transferred directly to a lyophilizer to remove the solvent while producing the final particles in the vial. The final particles can also be produced by addition of agents (salts, a second solvent, polymers, etc.) to decrease the solubility of the particles to produce a suspension of the particles. Thus the solids never have to be removed from the vial.

This method permits the production of particles with fine control of the size distribution by freezing liquid solutions of substances in thin uniform films at fast freezing rates inside vials. The method is implemented in three fundamental steps: (a) introducing a liquid solution of the substances inside a cylindrical vial; (b) immersing the cylindrical vial into a liquid coolant while rotating it horizontally until the liquid has frozen as a film in the vial's internal walls; (c) removal of the solvent by lyophilization or by extraction of the frozen solvent into a second solvent.

The first step begins by dissolving the active substances in an aqueous solution in typical concentrations ranging from 1 mg/ml to 500 mg/ml. This solution may also contain excipients including cryoprotectives or surfactants as an example. The solution is introduced into a cylindrical vial, where the liquid volume and the vial's dimensions determine the thickness of the final frozen film (important variables in the control of the size distribution). Table 14 shows an example of different film thicknesses obtained for vials of two different sizes.

TABLE 14

Film thicknesses obtained after freezing different volumes of liquid solution in vials of different dimensions.

| Vial 1<br>Internal Diameter 15 mm<br>Length 40 mm | | Vial 2<br>Internal Diameter 24 mm<br>Length 48 mm | |
|---|---|---|---|
| Liquid Volume (ml) | Film thickness (mm) | Liquid Volume (ml) | Film thickness (mm) |
| 1 | 0.6 | 1 | 0.3 |
| 2 | 1.2 | 2 | 0.6 |
| 3 | 1.8 | 3 | 0.9 |
| 5 | 3.5 | 5 | 1.5 |
| | | 10 | 3.2 |

Figure 18:
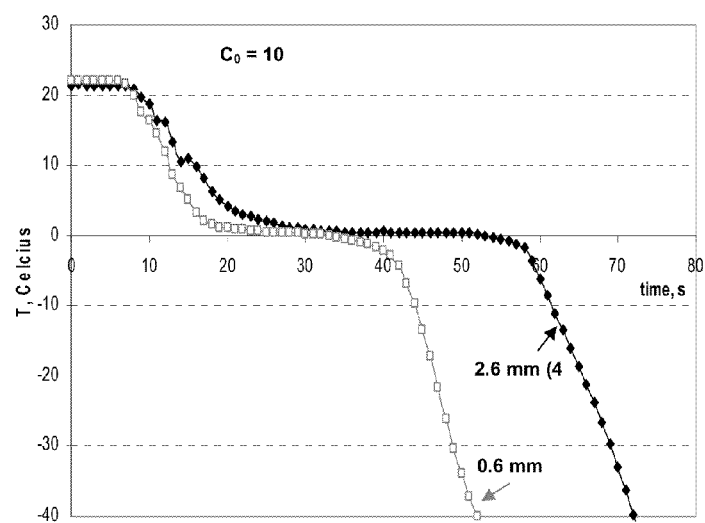
FIG. 18 Freezing temperature profiles of lysozyme solutions (10 mg/ml) inside vials.

The second step includes immersing the vial horizontally inside liquid coolant (e.g. liquid N2) while rotating it. The rotation causes the liquid solution to freeze as a film of uniform thickness in the cylindrical vial internal walls. The coolant temperature (typically ranging from 50K to 253K) and the rotation speed (typically ranging from 15 RPM to 600 RPM) may be adjusted to control the freezing rate. FIG. 18 show freezing temperature profiles measured for freezing different liquid volumes inside vials. The temperatures were measured with a type T thermocouple while processing with a coolant at 80 K and a rotation speed of 30 RPM.

Figure 19:
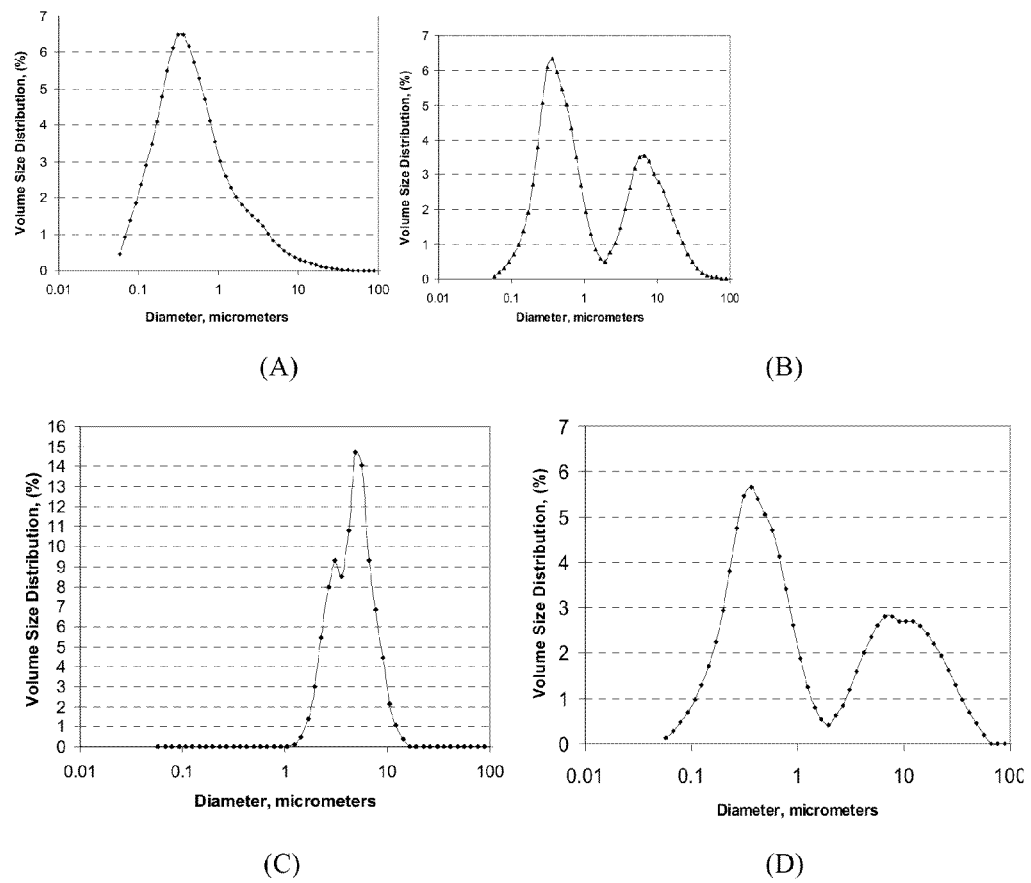

The third step is the removal of the solvent by lyophilization or adding agents to the frozen solvent to create a poorly-soluble environment producing a suspension. A second solvent, salts, polymers and other agents can be added to the aqueous based formulation to produce a poorly-soluble environment for the protein-based particles. Solvents are typically water-miscible organic solvents such as acetonitrile and ethanol. Salts, such as sodium sulphate and ammonium sulphate, and polymers such as PEG, cause a decrease in the solubility of the proteins in an aqueous environment, creating a suspension of particles. FIG. 19 shows typical particle size distributions obtained with the present method measured by a multi-angle laser light scattering with a Malvern Mastersizer-S with the particles suspended in acetonitrile. At selected conditions, nanometric particles, micrometric or bimodal distributions of particles of both size scales can be produced, as shown in FIG. 19. The size distribution is controlled by solutes concentration, the temperature of the liquid coolant, and the volume of the liquid and the vial rotating speed. Table 15 shows the process conditions that resulted in the particle size distributions shown in FIG. 19.

TABLE 15

Figure 13:
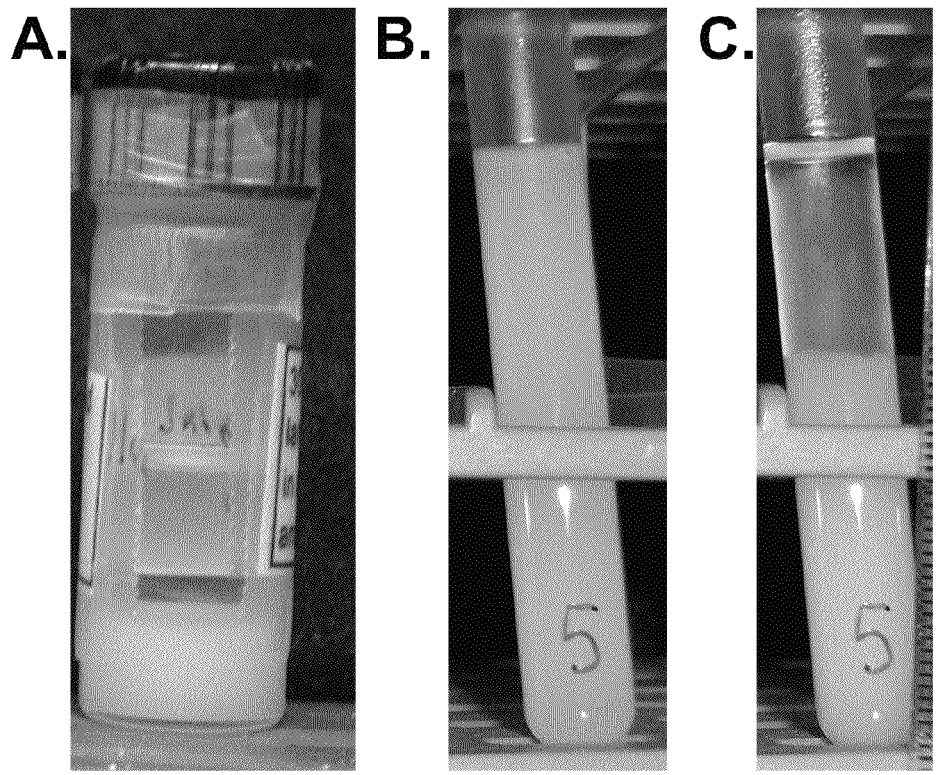
FIG. 13A-13C Pictures of the 300 mg/mL Lysozyme suspension in 50/50 Benzyl Benzoate and Safflower Oil.

Process conditions used in the production of particles by Film Freezing into Vials, corresponding to the size distributions shown in FIG. 13. The film thickness is defined as the maximum thickness of the final frozen mass within a vial in the horizontal position. The vial inside diameter is 15 mm.

| REF. in FIG. 7 | Protein Concentration mg/ml | Film Thickness mm | Rotation speed RPM | Coolant Temperature K |
|---|---|---|---|---|
| (a) | 20 | 2.6 | 30 | 80 |
| (b) | 10 | 0.6 | 30 | 80 |
| (c) | 5 | 2.6 | 120 | 80 |
| (d) | 5 | 0.6 | 30 | 210 |

Figure 20:
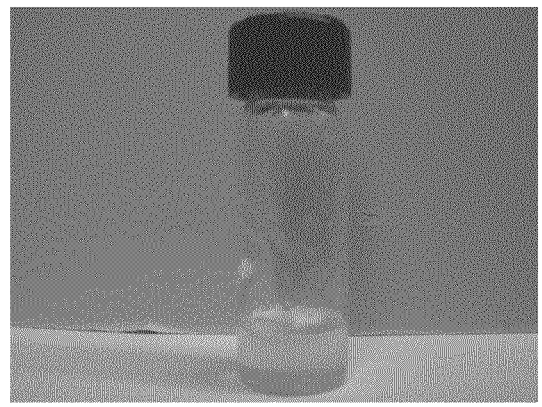
Figure 21:
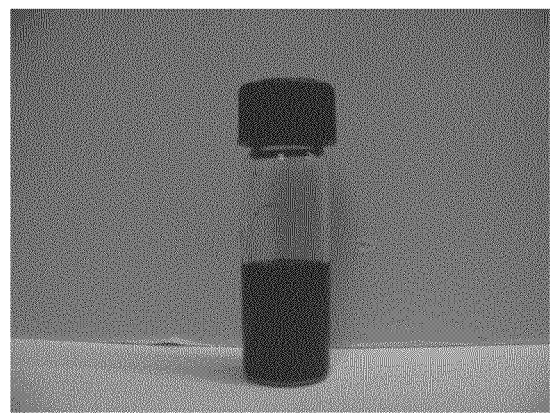

The following examples demonstrate protein suspensions made by film freezing of protein in a vial followed by lyophilization, and then suspension of the lyophilized material in a solvent with manual shaking. In FIG. 20, 4 ml of lysozyme solution (20 mg/ml) in water were frozen by Film Freezing inside the Vial. After lyophilization, a suspension with 80 mg/mL lysozyme was formed by adding benzyl benzoate. In FIG. 21, 2 ml of hemoglobin solution (150 mg/ml) in water was frozen by Film Freezing inside the Vial. The frozen solution was lyophilized and the particles were suspended in 2 ml of Benzyl Benzoate to make up a 150 mg/ml suspension. In both cases, the suspensions did not settle over 1 day, and could resuspended by manual shaking.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The invention claimed is:

1. A high concentration low viscosity suspension comprising:
 a pharmaceutically acceptable solvent;
 one or more sub-micron or micron-sized non-crystalline particles comprising one or more proteins or peptides; and
 one or more additives in the pharmaceutically acceptable solvent to form a high concentration low viscosity suspension with a concentration of at least 200 mg/ml and a solution viscosity of between 2 and 50 centipoise that is suspendable upon shaking or agitation, wherein upon delivery the one or more sub-micron or micron-sized peptides dissolves and do not form peptide aggregates or only a small fraction of aggregates.

2. The composition of claim 1, wherein the pharmaceutically acceptable solvent comprises a pharmaceutically acceptable aqueous solvent, a pharmaceutically acceptable non-aqueous solvent or combination.

3. The composition of claim 1, wherein the concentration of the high concentration low viscosity suspension is greater than 250, 300, 400, or 500 mg/mL, and the high concentration low viscosity suspension has a ratio of one or more additives to the one or more proteins or peptides that is less than 0.01, 0.05, 0.1, 0.2, 0.5, 1, 2, 2.5, 5, 7.5, 10, 12 or more and the high concentration low viscosity suspension has a viscosity of less than 40, 30, 20, or 10 centipoise.

4. The composition of claim 1, wherein the one or more proteins or peptides are selected from an antibody, one or more antibodies conjugated to a metal nanoparticle, one or more antibodies on a shape based composition, a growth factor, an antigen, a vaccine, an anti-inflammatory agent, a therapeutic polypeptide or peptide or a combination thereof.

5. The composition of claim 1, wherein the one or more submicron or micron-sized peptide particles have a volume average diameter of 30, 20, 10, 5, 2, 1 0.75, 0.5, 0.4, 0.3, 0.1, 0.05, or 0.02 micrometers.

6. The composition of claim 1, wherein the one or more additives are selected from the group consisting of a stabilizer, a surfactant, an emulsifier, a salt, an amino acid, a small peptide, a polypeptide, a protein, a polymer, a cosolvent, a sodium salt, a zinc salt, a lithium salt, a potassium salt, a ammonium salt, a calcium salt, a magnesium salt, a zinc salt, a chloride salt, a bromide salt, an iodide salt, a phosphate salt, a sulfate salt, a glycerol, an erythritol, an arabinose, a xylose, a ribose, an inositol, a fructose, a galactose, a maltose, a glucose, a mannose, a trehalose, a sucrose, a poly(ethylene glycol), a carbomer 1342, a glucose polymers, a silicone polymer, a polydimethylsiloxane, a polyethylene glycol, a carboxy methyl cellulose, a poly(glycolic acid), a poly(lactic-co-glycolic acid), a polylactic acid, a dextran, a poloxamers, organic co-solvents selected from ethanol, N-methyl-2-pyrrolidone, PEG 300, PEG 400, PEG 200, PEG 3350, Propylene Glycol, N,N Dimethylacetamide, N-methyl-2-pyrrolidone, dimethyl sulfoxide, solketal, tetahydrofurfuryl alcohol, diglyme, ethyl lactate and combinations thereof.

7. The composition of claim 1, wherein the one or more additives are part of the one or more sub-micron or micron-sized particles, the high concentration low viscosity suspension or both.

8. The composition of claim 1, wherein more than 0.5, 0.6, 0.7, 0.8, 0.9, 0.95, or 0.99 of the one or more proteins or peptides are not soluble as entities smaller than 30, 20, or 10 nm.

9. The composition of claim 1, wherein a relative monomer fraction of one or more proteins or peptides prior to the formation of the high concentration low viscosity suspension is greater than 0.7, 0.8, 0.9, 0.95, 0.97, 0.98, or 0.99 upon dissolution of the one or more proteins or peptides into a buffered aqueous media and a relative monomer fraction of one or more proteins or peptides in the high concentration low viscosity suspension is 0.93, 0.95, 0.96, 0.97, 0.98, 0.99, 0.995 the value of the monomer fraction upon dissolution of the peptides into a buffered aqueous media of the one or more micron-sized peptide particles.

10. The composition of claim 1, wherein the one or more sub-micron or micron-sized particles dissolve in a subject upon delivery in less than 1, 5, 10, 30, and 60 minutes.

11. The composition of claim 1, further comprising a time release agent to control the release of the one or more sub-micron or micron-sized particles over a time of between about 1 hour and 10 weeks.

12. The composition of claim 1, wherein a non-monomeric fraction of the one or more proteins or peptides is delivered at a concentration of less than 5%, 2%, 1%, 0.5%, 0.2%, or 0.1% of a total peptide weight.

13. A single dose high concentration low viscosity suspension comprising:
 a single dose container;
 a pharmaceutically acceptable solvent disposed in the single dose container, wherein the pharmaceutically acceptable solvent is selected from an aqueous solvent, a non-aqueous solvent or combination thereof;
 one or more sub-micron or micron-sized non-crystalline particles disposed in the single dose container, wherein the one or more sub-micron or micron-sized non-crystalline particles comprising one or more proteins or peptides; and
 one or more additives optionally disposed in the single dose container to form a high concentration low viscosity suspension with a concentration of at least 200 mg/ml and a solution viscosity of between 2 and 50 centipoise syringeable through a 21 to 27-gauge needle.

14. The composition of claim 1, wherein the concentration of the high concentration low viscosity suspension is greater than 300 mg/mL.

\* \* \* \* \*